(12) United States Patent
Morita et al.

(10) Patent No.: US 8,085,312 B2
(45) Date of Patent: Dec. 27, 2011

(54) IMAGE INPUT APPARATUS, IMAGE INPUT METHOD, PERSONAL AUTHENTICATION APPARATUS, AND ELECTRONIC APPARATUS

(75) Inventors: Nobuhiro Morita, Kanagawa (JP); Yuji Yamanaka, Kanagawa (JP); Toshiyuki Iseki, Kanagawa (JP); Toshimichi Nasukawa, Iwate (JP); Shinichi Kosuga, Iwate (JP); Hiroaki Takahashi, Iwate (JP); Akira Takahashi, Iwate (JP)

(73) Assignee: Ricoh Company, Ltd., Tokyo (JP)

( * ) Notice: Subject to any disclaimer, the term of this patent is extended or adjusted under 35 U.S.C. 154(b) by 506 days.

(21) Appl. No.: 12/096,625

(22) PCT Filed: Oct. 5, 2007

(86) PCT No.: PCT/JP2007/070025
§ 371 (c)(1),
(2), (4) Date: Jun. 9, 2008

(87) PCT Pub. No.: WO2008/044781
PCT Pub. Date: Apr. 17, 2008

(65) Prior Publication Data
US 2008/0316323 A1 Dec. 25, 2008

(30) Foreign Application Priority Data
Oct. 12, 2006 (JP) ................... 2006-278423

(51) Int. Cl.
*H04N 5/228* (2006.01)
(52) U.S. Cl. .............. 348/222.1; 348/335; 348/340; 382/115; 382/124; 382/125; 382/126; 359/20
(58) Field of Classification Search .......... 348/264, 348/222.1, 340
See application file for complete search history.

(56) References Cited

U.S. PATENT DOCUMENTS
5,193,124 A * 3/1993 Subbarao ............... 382/255
(Continued)

FOREIGN PATENT DOCUMENTS
EP 1 708 136 A1 10/2006
(Continued)

OTHER PUBLICATIONS

Shogenji, Rui et al., "Development of Thin Observation Module by Bound Optics", The Journal of the Institute of Image Information and Television Engineers, vol. 57, No. 9, pp. 1135-1141, 2003, (with English abstract).

(Continued)

*Primary Examiner* — Sinh Tran
*Assistant Examiner* — Paul Berardesca
(74) *Attorney, Agent, or Firm* — Oblon, Spivak, McClelland, Maier & Neustadt, L.L.P.

(57) ABSTRACT

An image input apparatus that inputs an image of an object residing within a living body is disclosed. The image input apparatus includes a light source that irradiates near infrared light on the living body, a lens array arranged at a position facing the living body and including plural lenses each having a face with zero or negative power arranged at a side facing the living body and a face with positive power arranged at a side facing an image surface, an imaging unit arranged at the image surface side of the lens array that forms a compound-eye image corresponding to a collection of ommatidium images formed by the lenses of the lens array, and a reconstruction unit that reconstructs a single image from the compound-eye image using a parallax between the ommatidium images. The reconstructed single image is input as the image of the object.

11 Claims, 15 Drawing Sheets

U.S. PATENT DOCUMENTS

| | | | |
|---|---|---|---|
| 5,818,956 A * | 10/1998 | Tuli | 382/126 |
| 2001/0050765 A1 | 12/2001 | Antonelli et al. | |
| 2002/0048014 A1 * | 4/2002 | Kono et al. | 356/71 |
| 2002/0075450 A1 * | 6/2002 | Aratani et al. | 351/206 |
| 2003/0086013 A1 * | 5/2003 | Aratani | 348/335 |
| 2004/0022421 A1 * | 2/2004 | Endoh et al. | 382/115 |
| 2004/0184641 A1 * | 9/2004 | Nagasaka et al. | 382/124 |
| 2004/0202354 A1 | 10/2004 | Togino | |
| 2004/0208346 A1 * | 10/2004 | Baharav et al. | 382/124 |
| 2005/0148876 A1 * | 7/2005 | Endoh et al. | 600/454 |
| 2005/0213102 A1 | 9/2005 | Morita | |
| 2005/0265585 A1 * | 12/2005 | Rowe | 382/124 |
| 2006/0055772 A1 | 3/2006 | Rosen | |
| 2007/0090275 A1 * | 4/2007 | Toyoda et al. | 250/208.1 |
| 2009/0074316 A1 * | 3/2009 | Morita et al. | 382/255 |
| 2009/0080709 A1 * | 3/2009 | Rowe et al. | 382/115 |

FOREIGN PATENT DOCUMENTS

| | | | |
|---|---|---|---|
| JP | 7 21373 | | 1/1995 |
| JP | 2001 61109 | | 3/2001 |
| JP | 2001 358904 | | 12/2001 |
| JP | 2002 218160 | | 8/2002 |
| JP | 2003 60916 | | 2/2003 |
| JP | 2003 163938 | | 6/2003 |
| JP | 2004 272821 | | 9/2004 |
| JP | 2004 305632 | | 11/2004 |
| JP | 2005 92375 | | 4/2005 |
| JP | 2005-176040 | | 6/2005 |
| JP | 3705766 | | 8/2005 |
| JP | 2006-135823 | * | 5/2006 |
| JP | 2007 74079 | | 3/2007 |
| JP | 2007 156749 | | 6/2007 |
| JP | 2007 158825 | | 6/2007 |
| JP | 2007 304525 | | 11/2007 |
| JP | 2007 312314 | | 11/2007 |
| JP | 2008 78692 | | 4/2008 |
| WO | 2005 017828 | | 2/2005 |

OTHER PUBLICATIONS

Chinese Office Action issued Nov. 11, 2010, in Patent Application No. 200780001552.2 (with English-language translation).

J.W. Duparre et al. "Topical Review; Micro-Optical Artificial Compound Eyes"; Bioinspiration & Biomimetics, Institute of Physics Publishing, Bristol, GB; vol. 1, No. 1; Mar. 1, 2006; pp. R1-R16; XP020111414; ISSN: 1748-3190; DOI: 10.1088/1748-3182/1/1/R01.

Supplementary European Search Report issued May 18, 2011, in Application No. EP 07 82 9760.

Chen Shanben, Lin Tao et al.; "Intelligentized Welding Robot Technology"; China Machine Press; 4 pages.

Office Action issued Jul. 21, 2011, in Chinese Patent Application No. 2007800015522 (with English Translation).

* cited by examiner

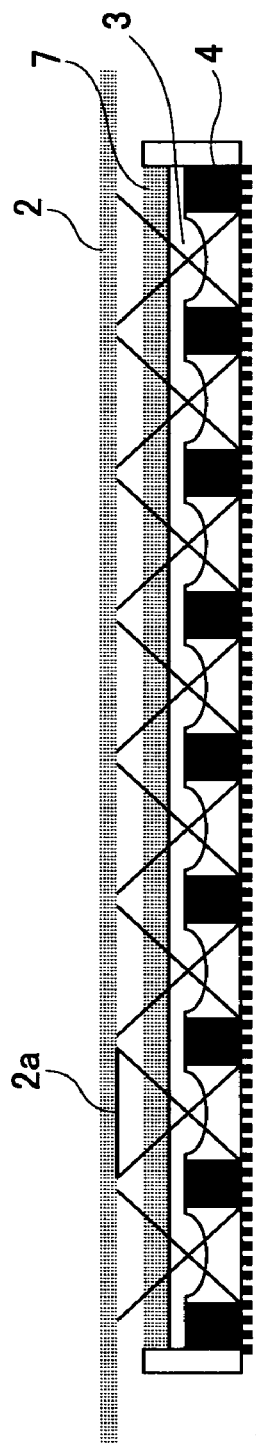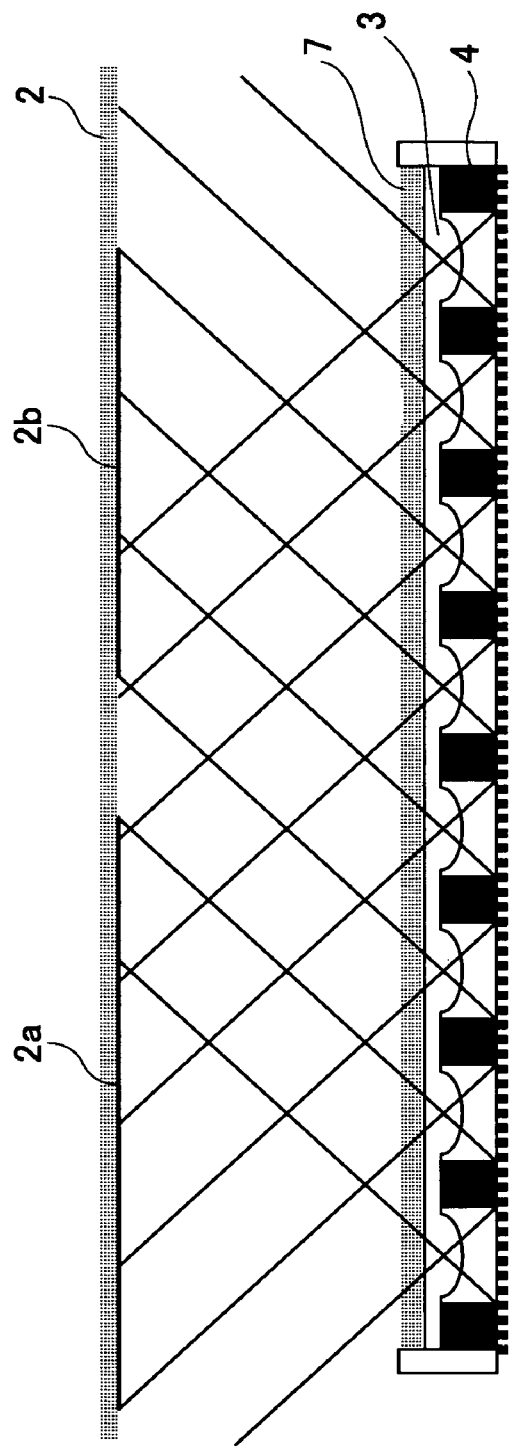

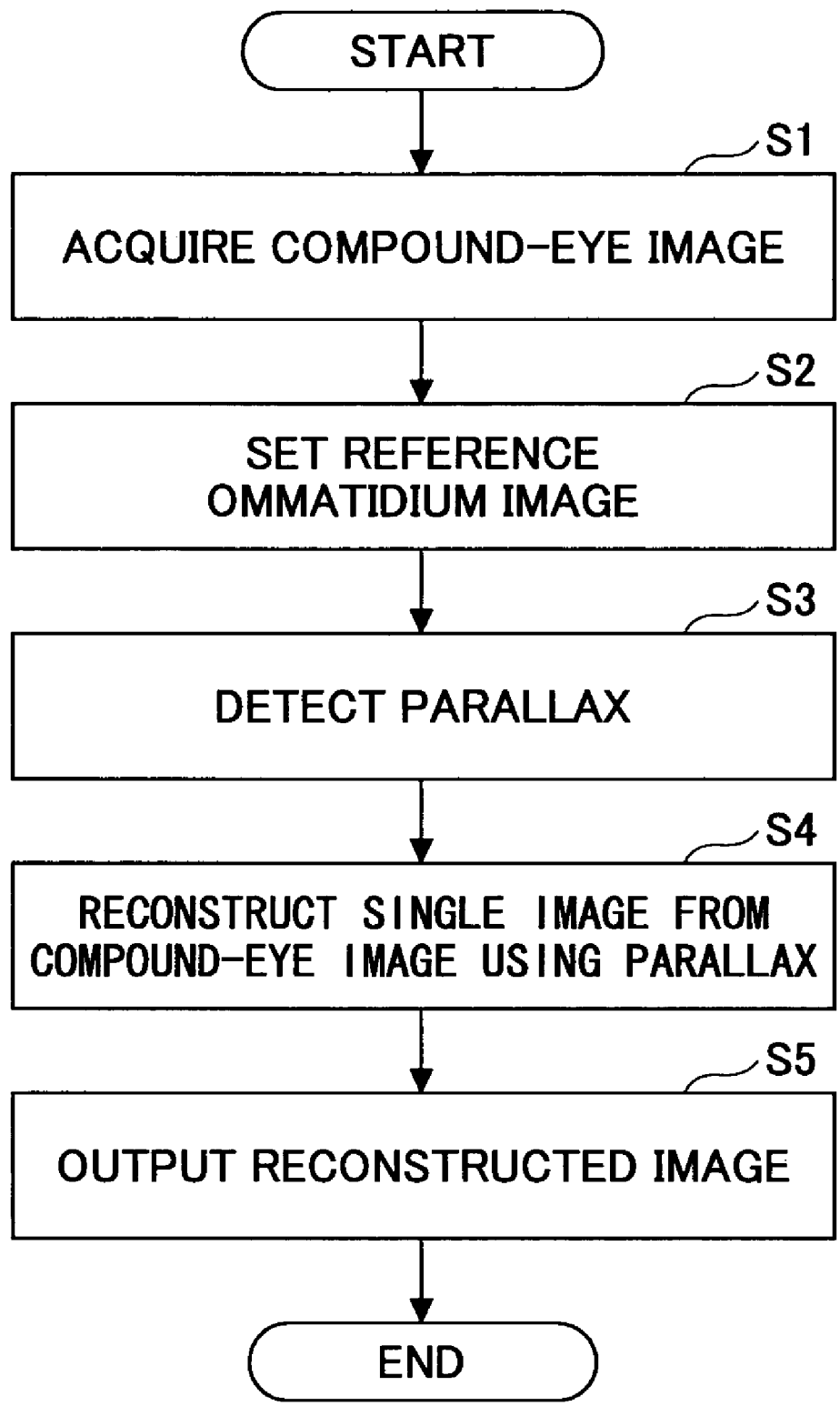

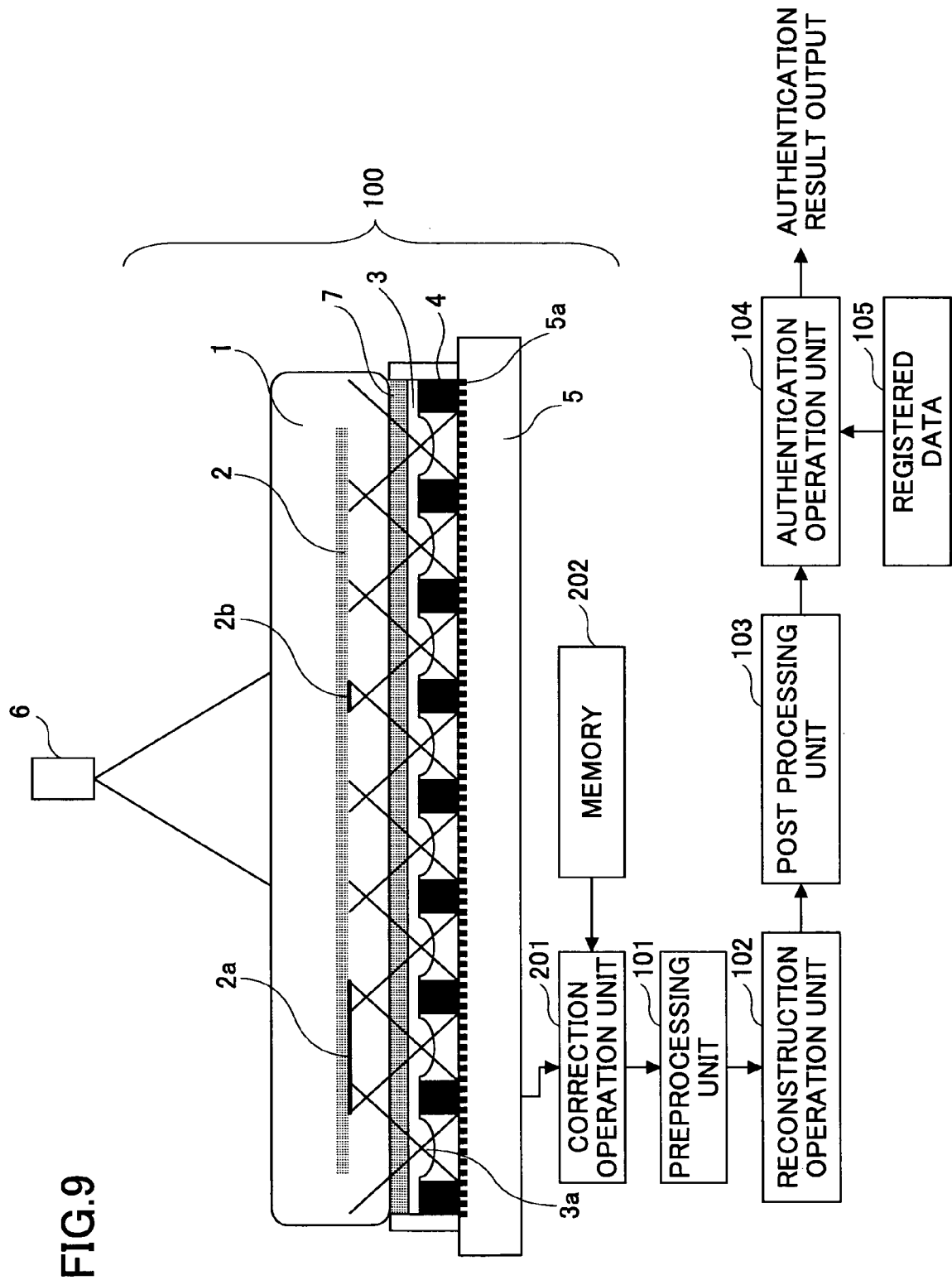

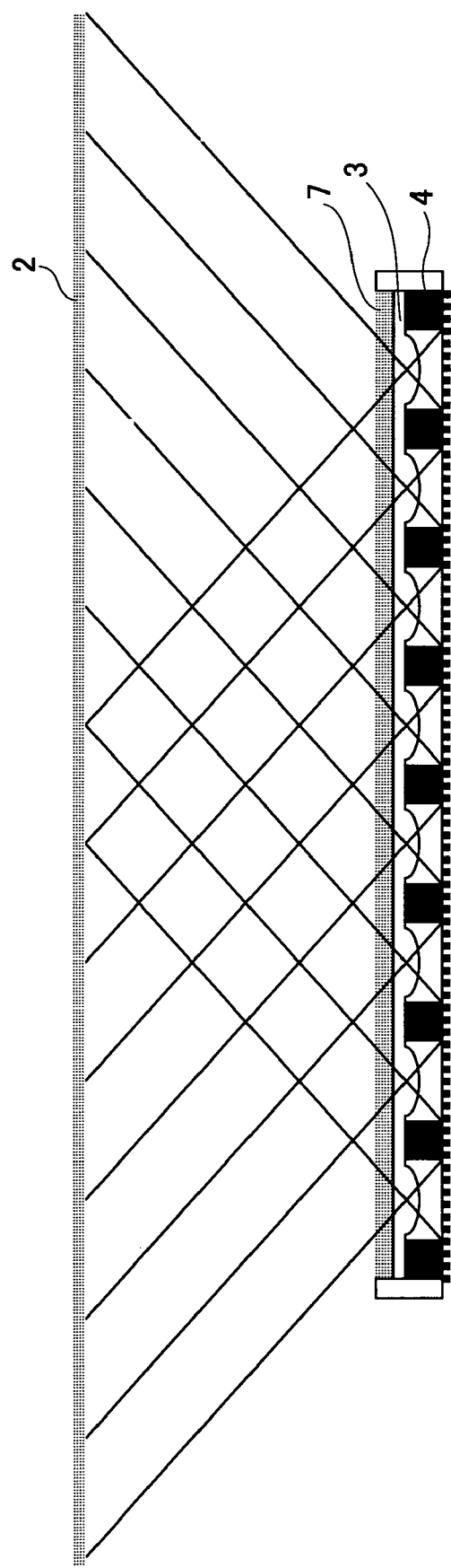

IMAGE INPUT APPARATUS, IMAGE INPUT METHOD, PERSONAL AUTHENTICATION APPARATUS, AND ELECTRONIC APPARATUS

TECHNICAL FIELD

The present invention relates to an input apparatus and an input method suitable for inputting an image of an object within a living body (e.g., veins of a finger, subdermal fingerprints), and a personal authentication apparatus that uses such the image of such an object.

BACKGROUND ART

Patent Document 1 (Japanese Laid-Open Patent No. 2004-27281), Patent Document 2 (Japanese Laid-Open Patent No. 2005-92375), and Patent Document 3 (Japanese Laid-Open Patent No. 7-21373) disclose embodiments of a personal authentication apparatus that irradiates infrared light or near infrared light on a finger to capture an image of a vein pattern within the finger and perform personal authentication based on the vein pattern.

Also, Patent Document 4 (Japanese Patent No. 3705766), Patent Document 5 (Japanese Laid-Open Patent No. 2001-61109), and Non-Patent Document 1 (Rui Shogenji et al., "Development of Thin Image Input Apparatus using Compound-Eye Optical System", The Journal of the Institute of Image Information and Television Engineers, Vol. 57, No. 9, pp. 1135-1141, 2003) disclose embodiments of a thin image input apparatus that uses a compound-eye optical system. Further, Non-Patent Document 1 discloses an exemplary fingerprint inputting technique to be applied to a fingerprint authentication system.

The personal authentication apparatuses disclosed in Patent Documents 1, 2, and 3 use single-eye optical systems for inputting the vein pattern image so that restrictions are imposed with respect to the object distance and imaging distance and the apparatus may not be adequately miniaturized. It is noted that in order to enable installation of a personal authentication apparatus in an electronic apparatus such as a mobile phone, a miniature information terminal such as a PDA, or a laptop computer, the personal authentication apparatus has to be adequately miniaturized.

To miniaturize the personal authentication apparatus, the image input apparatus for inputting the image of an object within a living body such the veins of a finger or subdermal fingerprints has to be miniaturized as well. As is noted in Patent Documents 4 and 5, in miniaturizing the image input apparatus, it is generally advantageous to use a compound-eye optical system. However, in the case of using the image input apparatus for personal authentication, the image of the object within a living body to be input and used for personal authentication has to be captured with adequate image quality in addition to miniaturizing the image input apparatus.

DISCLOSURE OF THE INVENTION

Aspects of the present invention are directed to providing a miniaturized (thin) image input apparatus that may be suitably used for inputting an image of an imaging object such as the veins or subdermal finger prints within a living body and a personal authentication apparatus using such an image input apparatus.

According to one aspect of the present invention, an image input apparatus is provided that inputs an image of an object residing within a living body, the apparatus including:

a light source that irradiates near infrared light on the living body;

a lens array that is arranged at a position facing the living body and includes plural lenses each having a face with zero or negative power arranged at a side facing the living body and a face with positive power arranged at a side facing an image surface;

an imaging unit that is arranged at the image surface side of the lens array and is configured to form a compound-eye image corresponding to a collection of ommatidium images formed by the lenses of the lens array; and a reconstruction unit that is configured to reconstruct a single image from the compound-eye image formed by the imaging unit using a parallax between the ommatidium images, the reconstructed single image being input as the image of the object.

According to another aspect of the present invention, an image input apparatus is provided that inputs an image of an object residing within a living body, the apparatus including:

a light source that irradiates near infrared light on the living body;

a lens array that is arranged at a position facing the living body and includes plural lenses each having a face with zero or negative power at a side facing the living body and a face with positive power at a side facing an image surface;

an imaging unit that is arranged on the image surface side of the lens array and is configured to form a compound-eye image corresponding to a collection of ommatidium images formed by the lenses of the lens array;

a correction unit that is configured to correct image degradation caused by the lenses in the ommatidium images of the compound-eye image formed by the imaging unit based on optical transfer function data pertaining to the lenses that are prepared beforehand and generate a corrected compound-eye image; and a reconstruction unit that is configured to reconstruct a single image from the corrected compound-eye image generated by the correction unit using a parallax between the ommatidium images, the reconstructed single image being input as the image of the object.

According to another aspect of the present invention, an image input method is provided for inputting an image of an object residing within a living body, the method including the steps of:

using an imaging optical system that includes a light source that irradiates near infrared light on the living body;

a lens array that is arranged at a position facing the living body and includes a plurality of lenses, each of the lenses having a face with zero or negative power at a side facing the living body and a face with positive power at a side facing an image surface; and an imaging unit that is arranged on the image surface side of the lens array and is configured to form a compound-eye image corresponding to a collection of ommatidium images formed by the lenses of the lens array;

correcting image degradation caused by the lenses in the ommatidium images of the compound-eye image formed by the imaging unit based on optical transfer function data pertaining to the lenses that are prepared beforehand to generate a corrected compound-eye image;

reconstructing a single image from the corrected compound-eye image using a parallax between the ommatidium images; and inputting the reconstructed single image as the image of the object.

BRIEF DESCRIPTION OF THE DRAWINGS

FIGS. 5A and 5B are diagrams illustrating a difference in the size of overlapping regions between adjacent ommatidium images according to a difference in the object distance;

FIG. 8 is a flowchart illustrating exemplary process steps for reconstructing a single image from a compound-eye image;

FIG. 9 is a diagram illustrating a second embodiment of the present invention;

FIG. 15 is a diagram illustrating an example of lowering the optical magnification and enlarging the field of view of an imaging optical system.

BEST MODE FOR CARRYING OUT THE INVENTION

Figure 1:
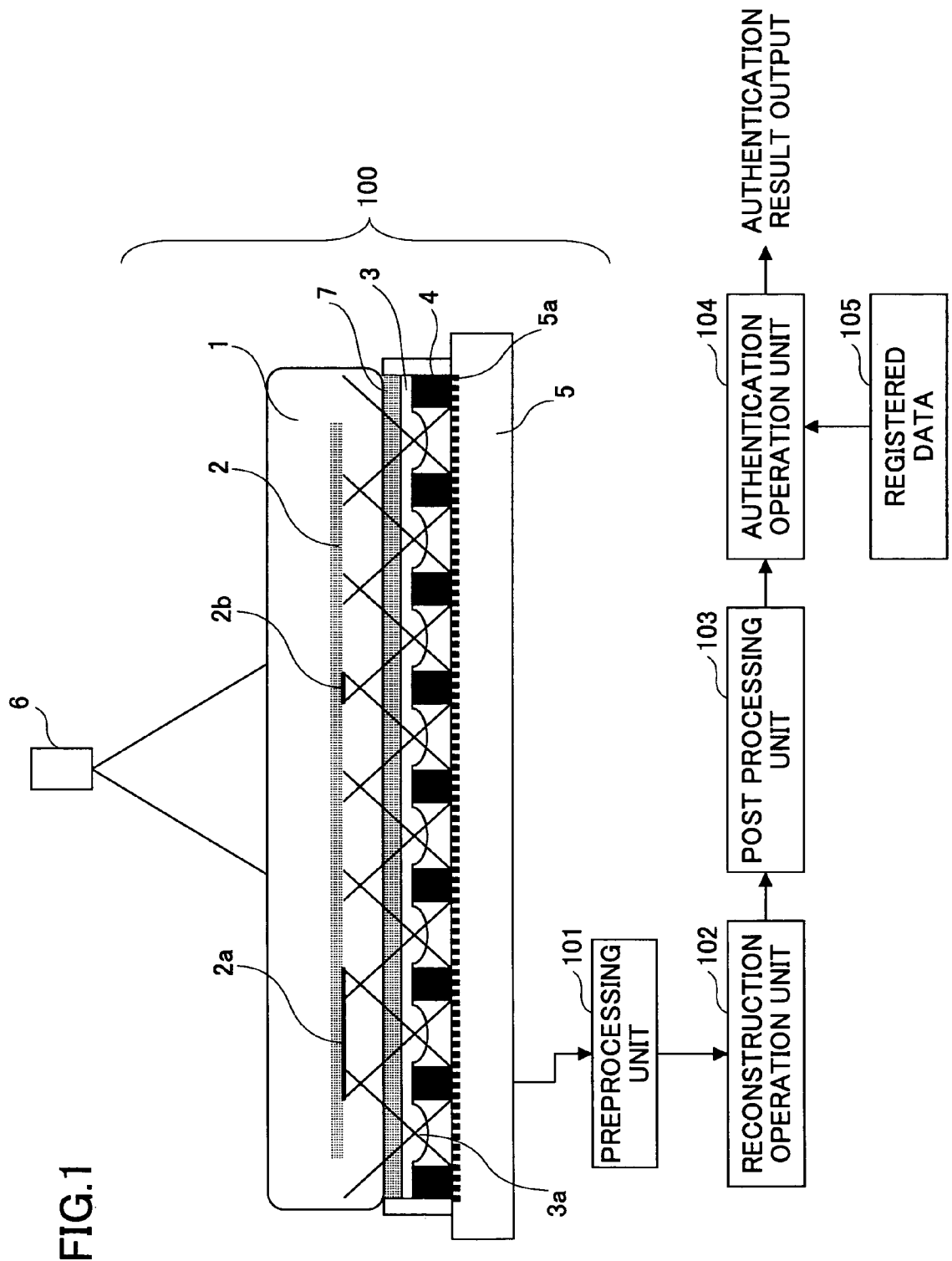
FIG. 1 is a diagram illustrating a first embodiment of the present invention.

In the following, preferred embodiments of the present invention are described with reference to the accompanying drawings. It is noted that in the examples described below, it is assumed that a human finger corresponds to a living body, and the internal veins of the finger correspond to the object to be imaged. Further, it is assumed that the image of the veins is input so that its vein pattern may be used to perform personal authentication. Also, in the drawings, component elements that are similar or substantially identical are given the same numerical references in order to reduce overlapping descriptions.

First Embodiment

FIG. 1 is a diagram showing an image input apparatus and a personal authentication apparatus according to a first embodiment of the present invention. In FIG. 1, an imaging optical system 100, a preprocessing unit 101, a reconstruction operation unit 102, and a post processing unit 103 make up an image input apparatus. Also, an authentication operation unit 104 and a registered data memory 105 make up an authentication process part that performs a personal authentication process based on a vein pattern. Such an authentication process part and an image input apparatus make up a personal authentication apparatus according to the present embodiment.

In FIG. 1, a finger (living body) 1 is placed on a certain location of the imaging optical system 100. The imaging optical system 100 captures an image of a vein 2 within the finger 1 as an object, and inputs the captured image. The imaging optical system 100 includes a light source 6, a lens array 3, a light shielding member 4, an image pickup device 5, and an optical band pass filter 7.

The lens array 3 is for forming the image of the object, and includes plural lenses 3a that are arranged into a two-dimensional array within a plane that is substantially perpendicular to the lens axis. However, the present invention is not limited to such an arrangement and the lenses 3a may alternatively be arranged into a one-dimensional array, for example.

According to an embodiment of the present invention, the lenses 3a making up the lens array 3 each have a face with a power of 0 or a negative power at the object side and a face with a positive power at the image surface side (i.e., lower face side). In the illustrated example of FIG. 1, a plano-convex lens with its convex face facing the image surface side is used as the lens 3a. It is noted that the convex face may be either a spherical surface or an aspheric surface. In the case where the convex face of the lens 3a is aspheric, design flexibility for improving the optical characteristics of the lens 3a may be enhanced.

The light shielding member 4 is for preventing crosstalk between light rays passing through the lenses 3a of the lens array 3 at the image surface and preventing generation of noise light such as ghost light and flared light. According to one embodiment, the light shielding member 4 is arranged to have a height extending from the lenses 3a of the lens array 3 to the image surface and includes openings (through holes) at the positions of the lenses 3a that are arranged into a two-dimensional array, each of the openings having a square cross-section. In another embodiment, the light shielding member may be a pin hole array having openings corresponding to the positions of the lenses 3a of the lens array 3. In yet another embodiment, the light shielding member may be made of a transparent parallel flat plate having openings corresponding to the lenses 3a of the lens array formed thereon and one or more non-transparent films deposited through vapor deposition, for example, on the upper face and/or lower face of the transparent parallel flat plate.

The image pickup device 5 is for forming a compound-eye image corresponding to a collection of images (ommatidium images) formed by the lenses 3a of the lens array 3. For example, a CCD image pickup device or a CMOS image pickup device having photo receiving elements 5a arranged into a two-dimensional array may be used. In one embodiment, the image pickup device 5 may include a circuit for adjusting the gain of a photoelectric transfer signal from the photo receiving element 5a and converting an analogue signal into a digital signal to be configured to output a captured image as digital image data. It is noted that the image pickup device 5 forms an image made up of plural pixels from the ommatidium images.

The light source 6 may be a light emitting diode (LED), for example, that irradiates near infrared light, which is absorbed at a relatively low absorption rate, on the finger (living body) 1. The near infrared light irradiated on the finger (living body) 1 by the light source 6 is absorbed by reduced hemoglobin within the veins (imaging object) 2 of the finger 1. However, the near infrared light is hardly absorbed by portions of the finger 1 other than the vein 2. In this way, the vein pattern may be visualized. Specifically, the vein pattern may be imaged on the imaging surface of the image pickup device 5 by the lenses 3a of the lens array 3 as a complex-eye image.

The optical band pass filter 7 only passes light within a predetermined wavelength range including the wavelength of the near infrared light irradiated by the light source 6. The optical band pass filter 7 is arranged to remove influences of noise light from light sources other than the light source 6. It is noted that the band pass filter 7 may not have to be included in a case where noise light does not have to be taken into consideration, or in a case where influences of noise light are removed by image data processing as is described below in relation to a fifth embodiment of the present invention. Also, in one embodiment, the optical band pass filter 7 may be arranged on the image surface side of the lens array 3 such as the imaging surface of the image pickup device 5.

It is noted that in the illustrated example of FIG. 1, only one light source 6 is shown. However, in other embodiments, plural light sources may be arranged to irradiate light on a region of the imaging object. Also, in one embodiment, a laser diode (LD) may be used as the light source 6. Further, it is noted that in the illustrated example of FIG. 1, the light source 6 is arranged to irradiate light on the finger (imaging object) 1 from a side not facing the lens array 3 (i.e., upper side of FIG. 1). However, in other embodiments, the light source 6 may be arranged to irradiate light on the finger 1 from the side or the bottom, for example. That is, since the near infrared light irradiated on the finger 1 is diffused in all directions within the finger 1, the vein pattern image of the finger 1 may be adequately captured in these embodiments as well. In another embodiment, a light conductor that guides the near infrared light generated at the light source 6 toward the finger 1 may be added.

The image pickup device 5 captures a compound-eye image of the vein pattern (object image) from the images formed by the lenses 3a of the lens array 3, and outputs the captured image as digital image data. The digital image data are preprocessed by the preprocessing unit 101 and transferred to the reconstruction operation unit 102. The preprocessing unit 101 may extract regions of the ommatidium images from the compound-eye image by removing shade portions created by the light shielding member 4 and performing a smoothing process or an averaging process on the individual ommatidium images; or extract the ommatidium images including the vein pattern and perform an emphasizing process on the ommatidium images for sharpening the vein pattern image, for example. The reconstruction operation unit 102 reconstructs a single image from the preprocessed ommatidium images by performing a reconstruction operation process using the parallax between the ommatidium images which is described in greater detail below. Then, post processing such as noise removal may be performed on the single image data by the post processing unit 103 as is necessary or desired after which the single image data are input to the authentication operation unit 104 as vein (object) image data. The above-described operations correspond to exemplary image input operations of the image input apparatus according to the present embodiment. It is noted that the above-described preprocessing and post processing operations correspond to processes to be performed before and after the image reconstruction process. Accordingly, the operations of the preprocessing unit 101 and the post processing unit 103 may be regarded as image reconstruction operations along with the operations of the reconstruction operation unit 102.

The authentication operation unit 104 may extract a characteristic amount of the vein pattern from the input vein image data and compare the extracted characteristic amount with a vein pattern of a registered person stored in the registered data memory 105 to conduct personal authentication, for example. Specifically, if the difference between the extracted characteristic amount and the registered characteristic amount of the registered person is less than or equal to a predetermined value, the person subject to authentication (i.e., owner of the finer 1) may be authenticated as the registered person. On the other hand, if the difference is greater than the predetermined value, authentication is denied. Since personal authentication techniques using a vein pattern are conventionally known, further detailed descriptions thereof are hereby omitted.

The lens array 3 may be made of transparent resin or glass material. The lens array 3 may be fabricated using a processing technique such as the reflow method, the area ration gray scale masking method, or the polishing method, for example. Alternatively, the lens array 3 may be fabricated through molding using a mold that is fabricated using the above processing techniques, for example. The light shielding member 4 may also be fabricated through similar processing using materials such as resin, glass, or metal. However, it is noted that the light shielding member 4 is arranged to prevent light from passing therethrough or being reflected thereon by using a nontransparent material or performing a coating process on a transparent material, for example.

Figure 2:
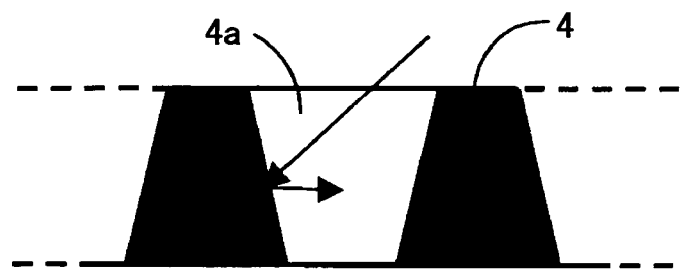
FIG. 2 is a diagram showing a light shielding member having a tapered opening.
Figure 3:
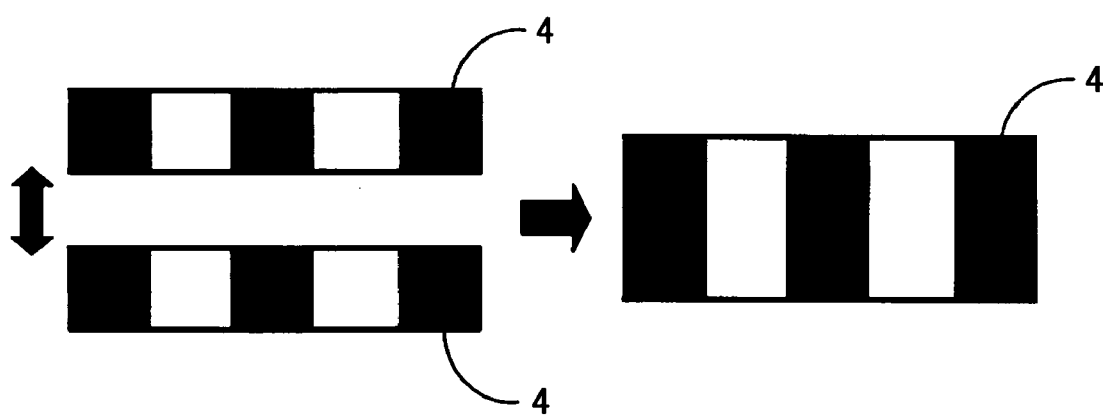
FIG. 3 is a diagram showing a light shielding member having a layered structure.

It is noted that in the illustrated example of FIG. 1, the opening (through hole) of the light shielding member 4 has substantially the same cross-sectional area across planes approximately orthogonal to the lens axis from the lens 3a to the imaging surface of the image pickup device 5. In an alternative embodiment as is shown in FIG. 2, the cross-sectional areas of the opening 4a may become smaller toward the imaging surface side so that the opening 4a may be arranged into a tapered structure. As is illustrated by the arrows shown in FIG. 2, by arranging the opening 4a into a tapered structure, light rays entering the opening 4a in a diagonal direction may be prevented from being reflected within the opening 4a and onto the imaging surface of the image pickup device 5 so that flares and ghosts may be prevented, for example. Also, it is noted that when the height of the light shielding member 4 has to be relatively high in accordance with the size of the opening 4a, processing of the light shielding member may become difficult. In such a case, the light shielding member 4 may be fabricated by layering plural layers having a suitable height for easy processing and bonding these layers together. FIG. 3 illustrates an example in which the light shielding member 4 is fabricated by layering two layers of the light shielding member 4 having a suitable height for easy processing.

Figure 4B:
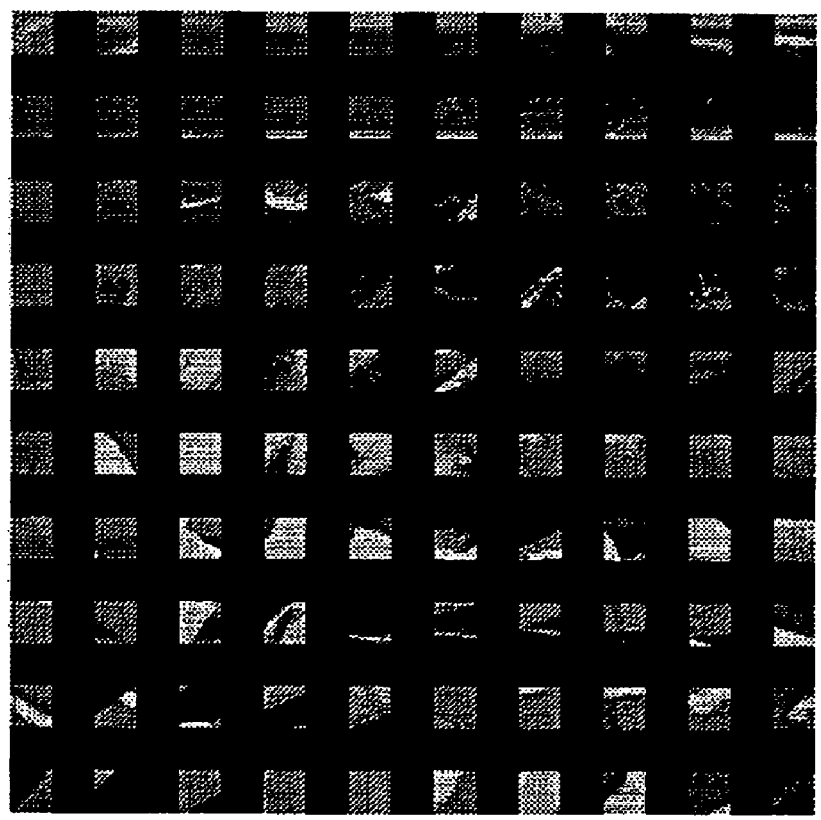
FIG. 4 is a diagram illustrating an exemplary simulation for generating a compound-eye image.
Figure 4A:

FIGS. 4A and 4B are diagrams illustrating a simulation example of forming a compound-eye image with the imaging optical system 100. FIG. 4A shows an original image from which a compound-eye image is formed. FIG. 4B shows the compound-eye image obtained from the original image of FIG. 4A. In the compound-eye image shown in FIG. 4B the black portions arranged between the ommatidium images correspond to shade portions formed by the light shielding member 4. The ommatidium images are formed by the lenses 3a of the lens array 3. Specifically, different portions of the imaging object are imaged according to the lens positions of the lenses 3a of the lens array 3. In FIG. 1, the region identified by the reference 2a represents the field of view of one lens 3a corresponding to a region to be observed and imaged as an ommatidium image by the lens 3a. Also, the regions identified by the reference 2b represent an overlapping portion at which the fields of view of two adjacent lenses 3a overlap one another. This portion corresponds to an overlapping region of adjacent ommatidium images of the compound-eye image shown in FIG. 4B.

It is noted that the distance from the skin surface of the finger to the vein varies depending on each person, and therefore, the distance from the lens array 3 to the vein 2 of FIG. 1 varies depending on the person being authenticated. When the distance between the vein 2 and the lens array 3 is reduced as is shown in FIG. 5A, or when the height of the light shielding member 4 is increased, the overlapping region between adjacent ommatidium images may not be created, for example. On the other hand, when the distance between the vein 2 and the lens array 3 is increased as is shown in FIG. 5B or when the height of the light shielding member 4 is reduced, the overlapping region between adjacent ommatidium images may be enlarged.

When there is no overlapping region between two adjacent ommatidium images, a single image may be reconstructed by extracting the individual ommatidium images within the compound-eye image, reorienting the extracted ommatidium images that are inverted by the lenses 3a to their original orientations, and simply connecting the reverted ommatidium images together. However, when overlapping regions exist between two adjacent ommatidium images, one of the overlapping regions becomes invalid so that in this case, when a single image is reconstructed by simply connecting together the ommatidium images, the size and the number of pixels making up the reconstructed image may be reduced and the image resolution may be decreased. Also, when the distance between the vein 2 and the lens array 3 increases as in the example of FIG. 5B, the area of overlapping regions and the number of invalid pixels increase and the optical magnification of the imaging optical system decreases so that the vein pattern image becomes smaller and the image resolution is lowered.

An embodiment of the present invention is directed to compensating for such a decrease in the image resolution due to an increase in the number of invalid pixels and a decrease in the optical magnification, for example, by performing a single image reconstruction process using the parallax between ommatidium images at the reconstruction operation unit 102 as is described below.

It is noted that a parallax exists between the ommatidium images due to the positional relationship between the lenses 3a and the vein (imaging object) 2. Thus, the ommatidium images correspond to images that are shifted according to the parallax. In the following descriptions, a parallax between ommatidium images refers to the shift amount (in length units) of a given ommatidium image with respect to a reference ommatidium image within a compound-eye image. Using the parallax between the ommatidium images, an image of an object structure buried in the pixels of ommatidium images may be reproduced. In one example, the parallax between the ommatidium images may be detected through calculating the sum of squares of the luminance difference between the ommatidium images using the below formula (1).

$$E = \sum_{x=1}^{X} \sum_{y=1}^{Y} \{I_B(x, y) - I_m(x - P_x, y - P_y)\}^2 \quad (1)$$

Figure 6:
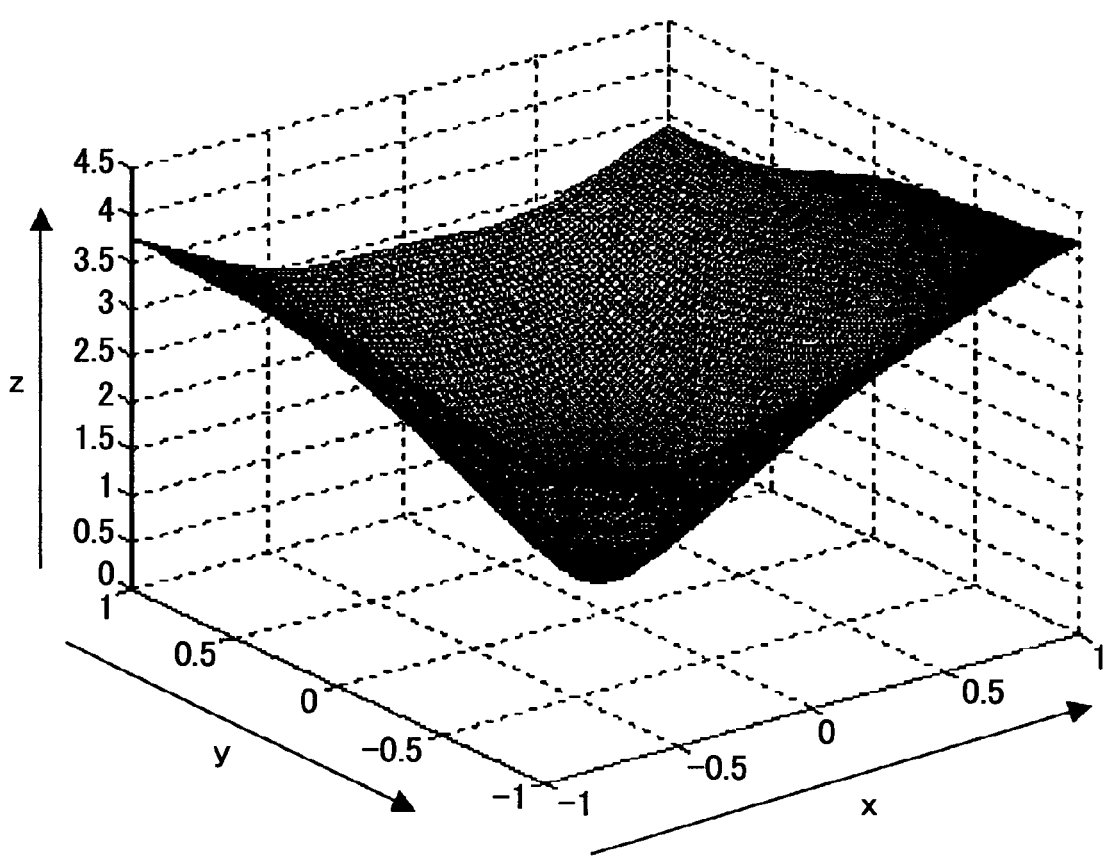
FIG. 6 is a graph illustrating variations in the sum E of squared values of the pixel luminance difference between ommatidium images according to variations in the parallax of the ommatidium images.

In the above formula (1), $I_B$ denotes the reference ommatidium image of the compound-eye image that may be arbitrarily set to be used as a reference based on which the parallaxes of the individual ommatidium images are obtained. $I_m$ denotes the individual ommatidium images, m denotes a number identifying the individual ommatidium images that may be a value ranging from 1 to N (N representing the number of lenses 3a making up the lens array 3). $P_x$ and $P_y$ denote parallaxes in the x and y directions, respectively, of a given ommatidium image with respect to the reference ommatidium image. According to the present example, the luminance difference between the given ommatidium image and the reference ommatidium image is obtained for all pixels making up the ommatidium images, and the sum E of the squared values of the luminance differences are obtained. The value E is successively calculated while gradually changing the values of $P_x$ and $P_y$, and the values of $P_x$ and $P_y$ when the value E takes a minimum value are determined as values representing the parallaxes in the x and y directions, respectively, with respect to the reference ommatidium image. FIG. 6 is a three-dimensional graph illustrating the change in the value of E in relation to the changes in the values of $P_x$ and $P_y$, the x axis representing the value of $P_x$, the y axis representing the value of $P_y$, and the z axis representing the value of E.

As can be appreciated from the graph of FIG. 6, the values of $P_x$ and $P_y$ when E takes a minimum value correspond to the parallaxes in the x and y directions, respectively, for the ommatidium image $I_m$ with respect to the reference ommatidium image $I_B$. In the case where the parallax dimension may be smaller than the pixel size of the image pickup device 5, the ommatidium image may be enlarged so that the parallax dimension corresponds to the pixel size of the image pickup device 5 or an integer multiple thereof. That is, the number of pixels making up the ommatidium image may be increased, and the parallax may be obtained by determining the minimum sum of squares of the luminance difference between the enlarged ommatidium images. To enlarge the ommatidium images, interpolation operation has to be implemented that involves determining the luminance of each pixel by referring to its adjacent pixel. As for the rate of expansion, since an approximate value of the parallax may be estimated from the optical magnification, the lens pitch of the lens array 3, and the pixel size of the image pickup device 5, the rate of expansion may be determined so that the estimated parallax may correspond to the pixel size of the image pickup device 5. In the case where the lens pitch processing accuracy of the lens array 3 is adequately high, the parallax of the ommatidium images may be geometrically calculated if the distance between the object and the lens array 3 is known. In this respect, according to one example, the parallax of the ommatidium images may be obtained by detecting the parallax between one pair of ommatidium images and calculating the below formula (2), in which δ denotes the parallax of a given ommatidium image, Δ denotes the parallax of the ommatidium image that is actually detected, N denotes the distance between the center of the ommatidium image for which the parallax has been detected and the center of the reference ommatidium image with respect to the x or y direction (horizontal or vertical direction) within an image, and n denotes the distance between the center of the given ommatidium image and the center of the reference ommatidium image.

$$\delta = \frac{\Delta \cdot n}{N} \quad (2)$$

In a case where the distance between the imaging object and the lens array 3 is relatively short so that the parallax between ommatidium images is relatively large, it may be preferable to detect parallaxes between adjacent ommatidium images rather than fixing a reference ommatidium image. In such a case, one of a pair of adjacent ommatidium images becomes the reference ommatidium image and the other becomes the ommatidium image for which the parallax is detected. As is mentioned above, there may be one or more ommatidium images that do not contain images of the vein pattern. Accordingly, in one preferred embodiment, the ommatidium images containing images of the vein pattern may be extracted in a preprocessing operation, and parallaxes may be detected for the extracted ommatidium images while the parallaxes for the rest of the ommatidium images without the images of the vein pattern may be obtained by calculating the above formula (2) using the detected parallaxes of the extracted ommatidium images. In another embodiment, the parallaxes of the ommatidium images may be detected by performing cross correlation calculation between the ommatidium images instead of calculating the sum of squares of the luminance differences between the ommatidium images.

Figure 7:
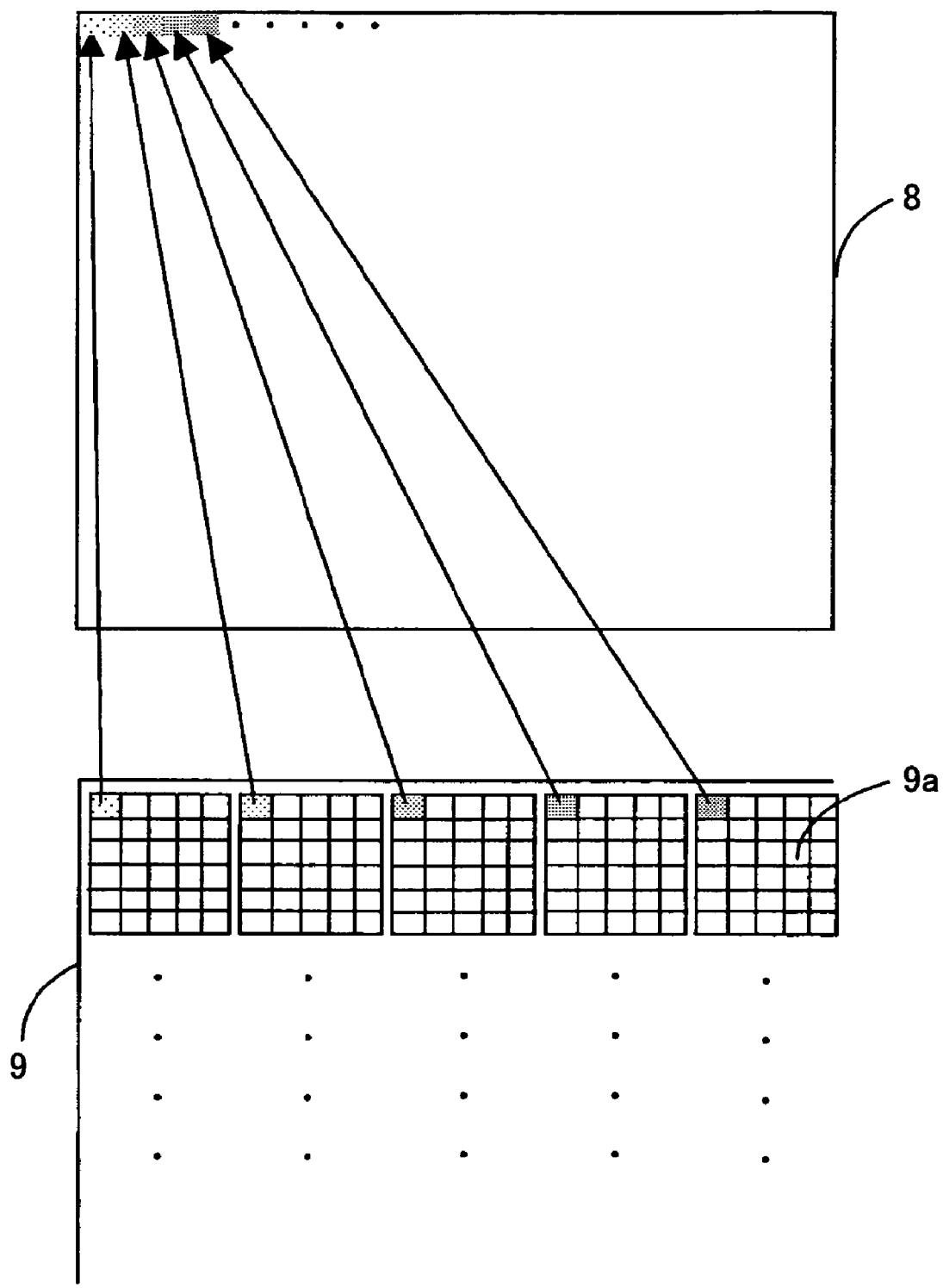
FIG. 7 is a diagram illustrating a method of arranging pixels in a process of reconstructing a single image from a compound-eye image.

FIG. 7 is a diagram illustrating a method of reconstructing a single image. In the illustrated example of FIG. 7, the pixel luminance is extracted from each ommatidium image 9*a* of a compound-eye image 9, and the extracted pixel luminance is arranged at a corresponding position of a reconstructed image 8 within a virtual space which position is determined based on the position of the ommatidium image 9*a* within the compound-eye image 9 and its parallax. By performing the above process of arranging the pixel luminance for all the pixels of the ommatidium images, a reconstructed image 8 may be obtained.

It is noted that when there are pixels that do not contain luminance within the reconstructed image owing to influences of the parallax dimension and/or shaded portions created by the light shielding member 4, for example, interpolation may be performed on such a pixel based on the luminance of its adjacent pixel. Also, in a case where the parallax is smaller than the pixel size, the reconstructed image is enlarged so that the parallax dimension may be equal to the pixel size or an integer multiple thereof. That is, the number of pixels making up the reconstructed image is increased, and the above-described process of arranging the pixel luminance may be performed thereafter.

FIG. 8 is a flowchart illustrating exemplary process steps that may be performed by the reconstruction operation unit 102. According to FIG. 8, first, the reconstruction operation unit 102 acquires a compound-eye image (step S1). Then, a reference ommatidium image for parallax detection is selectively set from the ommatidium images containing images of the vein pattern that are extracted in a preprocess (step S2), and parallaxes of individual ommatidium image with respect to the reference ommatidium image are detected (step S3). However, it is noted that parallaxes may not be detected for the ommatidium images that do not contain images of the vein pattern, and the parallaxes of such ommatidium images may be obtained by calculating the above formula (2), for example. Then, reconstruction operation is performed for constructing a single image from the compound-eye image using the parallaxes of the individual ommatidium images (step S4) after which the reconstructed single image is output (step S5). By performing such a reconstruction process, an image of an object structure that is buried in the pixels of the ommatidium images may be reproduced, and even when the distance between the object and the lens array 3 is increased and the resolution is decreased, a single image with improved resolution may be obtained.

It is noted that when the overlap between ommatidium images is relatively small, the detected parallax may be a very small value or an abnormal value, for example. In this respect, a threshold value for the parallax may be set, and the parallax to be used may be compared with the threshold value in step S4, for example. If the parallax is less than the threshold value, a single image may be reconstructed by simply reorienting the ommatidium images to their original orientations and connecting the ommatidium images together. On the other hand, if the parallax is greater than or equal to the threshold value, the above-described reconstruction process using the parallax may be performed.

In order to adequately perform the above-described reconstruction process using the parallax between ommatidium images provided that the distance between an object and the lens array 3 is within a predetermined permissible range, a given pair of adjacent ommatidium images that are imaged by the image pickup device 5 must have at least one pixel image in common representing the same portion of the object. Accordingly, design measures have to be implemented to ensure that adjacent images always have overlapping regions when the distance between the object and the lens array is within the predetermined permissible range. For example, the height of the light shielding member 4 and the distance between the lenses 3*a* of the lens array 3 may be properly adjusted so that adjacent ommatidium images may always have overlapping regions even when the distance between the object and the lens array 3 is at the minimum value of the predetermined permissible range. In another example, a transparent plate (not shown) for adjusting the distance between the object and the lens array 3 may be arranged between the finger (living body) 1 and the lens array 3, on the upper face of the optical band pass filter 7, for example, in order to prevent the distance from becoming smaller than the minimum value of the predetermined permissible range. In yet another example, when the optical band pass filter 7 is not provided, such a transparent plate may be arranged in place of the optical band pass filter 7. By implementing such measures, a compound-eye image that includes overlapping regions may always be obtained so that the reconstruction process may not have to be switched according to the results comparing the parallax to the threshold value as is described above. Also, since variations in the distance between the object and the lens array 3 may be reflected in the parallax, the reconstruction process according to an embodiment of the invention that uses the parallax may easily reflect such variations in the distance caused by differences in the thickness of the skin, for example.

It is noted that an exemplary case of inputting the vein pattern of a finger and using the vein pattern to perform personal authentication is described above. However, the present invention is not limited to such an example, and in other embodiments, a vein pattern of the palm or a finger print pattern of the finger may be imaged to perform personal authentication. In further embodiments, the present invention may be applied to imaging techniques for obtaining biological system image information to be used for non-invasive blood sugar level measurement, for example.

As is shown in FIG. 15, by reducing the back focus of the lens array 3, the optical magnification may be lowered and a wider field of view may be secured. In a case where the size of the object is relatively large, a general purpose image pickup device may not be capable of adequately imaging the object so that a dedicated image pickup device may have to be used which may raise the overall cost of the apparatus. Thus, in order to prevent such a cost increase, according to one preferred embodiment, a suitable optical magnification may be set based on the object size and the size of the general purpose image pickup device so that the overall image of the object may be adequately imaged using the general purpose image pickup device. It is noted that FIG. 15 illustrates a case where the optical magnification is reduced by adjusting the lens array 3; however, other measures may be implemented such as adding another optical system for de-magnifying the object image, for example.

Second Embodiment

FIG. 9 is a diagram illustrating an image input apparatus and a personal authentication apparatus according to a second embodiment of the present invention. The apparatus according to the present embodiment differs from that of the first embodiment in that it includes a correction operation unit 201 and a memory 202 as a correction processing part for correcting (e.g., through MTF correction) image degradation caused by the lenses 3a of the lens array 3. It is noted that other features of the apparatus according to the present embodiment may be substantially identical to the first embodiment. It is noted that optical transfer function (OTF) data pertaining to the plano-convex lens 3a having its convex face facing the image surface are stored in the memory 202 beforehand.

Figure 10B:
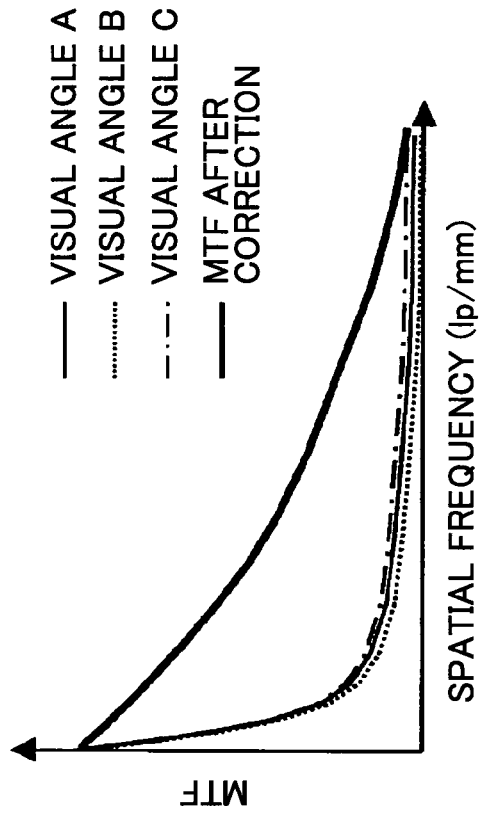
FIGS. 10A and 10B are graphs illustrating MTF characteristics of a plano-convex lens in relation to the object visual angle in a case where the convex face of the plano-convex lens faces the object side and a case where the convex face faces the image surface side.
Figure 10A:
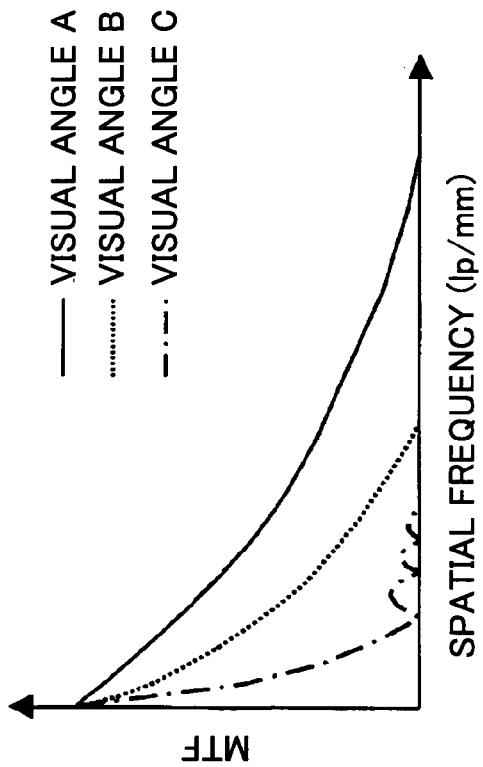

FIGS. 10A and 10B are graphs illustrating the relationship between the MTF corresponding to the gain of the optical transfer function of a plano-convex lens and the visual angle of an object in a case where the convex face of the plano-convex lens faces the object side and in a case where the convex face of the plano-convex lens faces the image surface side.

FIG. 10A shows the MTF characteristics of a plano-convex lens that has its convex face facing the object side, and FIG. 10B shows the MTF characteristics of a plano-convex lens that has its convex face facing the image surface side as with the lens 3a used the present embodiment. It is noted that the thin solid lines, dotted lines, and dashed lines shown in FIGS. 10A and 10B illustrate different angles of light rays incident to the lens; that is, the lines illustrate different visual angles of the object. Also, the thick solid line shown in FIG. 11B illustrates MTF characteristics after correction.

As is shown in FIG. 10A, in the case where the convex face of the plano-convex lens faces the object side, although relatively high MTF values may be obtained up to a relatively high spatial frequency band at certain visual angles, the MTF and the cutoff frequency vary significantly depending on the visual angle and the image may be prone to degradation. For example, to maintain a high MTF and a high cutoff frequency throughout a permissible visual angle range in this case, the permissible visual angle range may have to be very narrow and/or the lens may be required to have a complicated structure such as a layered structure or an aspheric structure, for example. In other words, it may be difficult to achieve adequate performance throughout a wide range of visual angles with a simple lens configuration in this case. It is noted that if the MTF can be limited within a predetermined range, the MTF characteristics may be improved through correction operation. However, in the case of FIG. 10A, since the MTF varies significantly depending on the visual angle, correction may have to be separately performed for different visual angles so that the processing load for performing the correction may be rather large. Also, since the MTF may easily drop to 0 at certain visual angles, the range of visual angles on which correction may be performed may be rather limited.

On the other hand, as is shown in FIG. 10B, in a case where the convex face of a plano-convex lens faces the image surface side as with the lens 3a used in the present embodiment, although the overall MTF level may be decreased, variations in the MTF with respect to variations in the visual angle may be reduced and variations in the cutoff frequency may also be reduced. Thus, in the case of performing MTF correction operation, the convex face of a plano-convex lens is preferably arranged to face the image surface side and the convex face configuration is preferably adjusted so that the MTF may be uniform and limited within a predetermined range in order to maintain MTF performance throughout a relatively wide range of visual angles with a relatively small processing load. For example, the MTF characteristics represented by the thick solid line shown in FIG. 10B may be easily achieved with the present configuration. In addition to achieving improvements in MTF characteristics as is described above, it is noted that in-plane errors such as distortions and curvatures may be reduced by arranging the convex face of a plano-convex lens to face the image surface side. Also, the above-described advantageous effects may be equally obtained in the case of using a lens having a lens face with a negative power at the object side and a lens face with a positive power at the image surface side.

In the following, the MTF correction process performed by the correction operation unit 201 is described. It is noted that the correction operation unit 201 according to the present embodiment is configured to perform a process of extracting ommatidium images of a compound-eye image formed by the image pickup device 5 while excluding shade portions created by the light shielding member 4 before performing the correction process. Thus, in the present embodiment, the preprocessing unit 101 does not have to perform the process of extracting the ommatidium images other than the shade portions.

The image of an object that has been degraded by the lens 3a, that is, the intensity data of each individual ommatidium image of a compound-eye image may be expressed by the below formula (3):

$$I(x,y) = FFT^{-1}[FFT\{S(x,y)\} \cdot OTF(x,y)] \quad (3)$$

It is noted that in the above formula (3), x and y denote position coordinates of an ommatidium image, I denotes the intensity data of an ommatidium image, S denotes intensity data of the object, OTF denotes optical transfer function data of the lens 3a, FFT denotes a Fourier transfer operator, and $FFT^{-1}$ denotes an inverse Fourier transfer operator. It is noted that the optical transfer function data OTF of the lens 3a may be obtained through autocorrelation of the pupil function of the lens 3a the using wave aberration data of the lens 3a obtained during the lens design stage.

The correction operation unit 201 uses the optical transfer function data OTF of the lens 3a that are calculated and stored in the memory 202 beforehand and performs computation of the below formula (4) on each ommatidium image of the compound image to correct image degradation caused by the lens 3a and generate an ommatidium image with improved MTF (and a compound-eye image corresponding to a collection of the corrected ommatidium images). It is noted that in the below formula (4), R denotes the intensity data of an ommatidium image after correction, α denotes a constant for preventing division by zero or noise amplification.

$$R(x, y) = FFT^{-1}\left[\frac{FFT\{I(x, y)\}}{OTF(x, y) + \alpha}\right] \quad (4)$$

It is noted that when the optical transfer function does not change according to the change in the light ray angle, this means that the optical transfer function may not change even when the lens itself is slightly tilted, for example. Therefore, influences of lens positioning errors upon installing the image pickup device 5 may be reduced in such as case. Also, it is noted that when the light focusing performance level of the lens is high, the focal point may easily spread to cause image degradation even with a slight deviation of the image surface position with respect to the optical axis. However, in a case where the light focusing performance level of the lens is relatively low as in the example of FIG. 10B, the focal point may be prevented from spreading very far when the image surface position is slightly deviated from the optical axis. In this way, influences of errors in setting the distance between the lens and the image surface may be reduced, for example. Further, in a preferred embodiment, the lens array 3 may be coupled to the light shielding member 4 upon assembling the apparatus. Specifically, the convex faces of the lenses 3a facing the image surface side may engage corresponding openings (through holes) of the light shielding member 4 so that alignment of the lens array 3 and the light shielding member 4 may be facilitated, for example.

It is noted that a correction process that involves frequency filtering using FFT is described above as an illustrative example. However, a similar correction process may be performed through de-convolution using a point-spread function pattern, for example. It is noted that a process using a point-spread function pattern may be simpler than that using FFT (fast Fourier transform) so that the cost of the overall apparatus may be reduced in the case of fabricating a dedicated processing circuit, for example. In another preferred embodiment, optical transfer function data for correction operation may be calculated for each of plural visual angles and stored in the memory 202 beforehand so that correction may be performed using corresponding optical transfer function data for each of image regions corresponding to the different visual angles. In a further embodiment, correction may be performed on in-plane errors such as curvatures and distortions by estimating their error levels beforehand.

According to one modified example of the embodiment shown in FIG. 9, the correction processing part for correcting image degradation caused by the lens 3a (MTF correction) may be arranged to come after the post processing unit 103 rather than before the preprocessing unit 101. Specifically, a correction operation unit may be arranged between the post processing unit 103 and the authentication operation unit 104, and a memory for storing optical transfer function data may be connected to this correction operation unit so that image degradation correction (MTF correction) may be performed on a reconstructed single image. It is noted that correction process with respect to a single image may be completed by performing one correction process sequence on the reconstructed single image so that operation time may be reduced compared to the case of performing correction on each ommatidium image. However, it is noted that since the optical transfer function data to be used in the correction process pertain to the individual lenses 3a and are intended to be used for correcting the individual ommatidium images, when the correction process is performed on the single image rather than the individual ommatidium images, correction errors may inevitably be increased compared to the case of performing correction on the individual ommatidium images.

Third Embodiment

It is noted that the optical transfer function of a lens may vary depending on the object distance (i.e., distance from the object 2 to the lens array 3). Particularly, in an imaging optical system of an image input apparatus according to an embodiment of the present invention where the object is positioned relatively close to the lens array 3, the optical transfer function may greatly vary in response to variations in the object distance.

Figure 11:
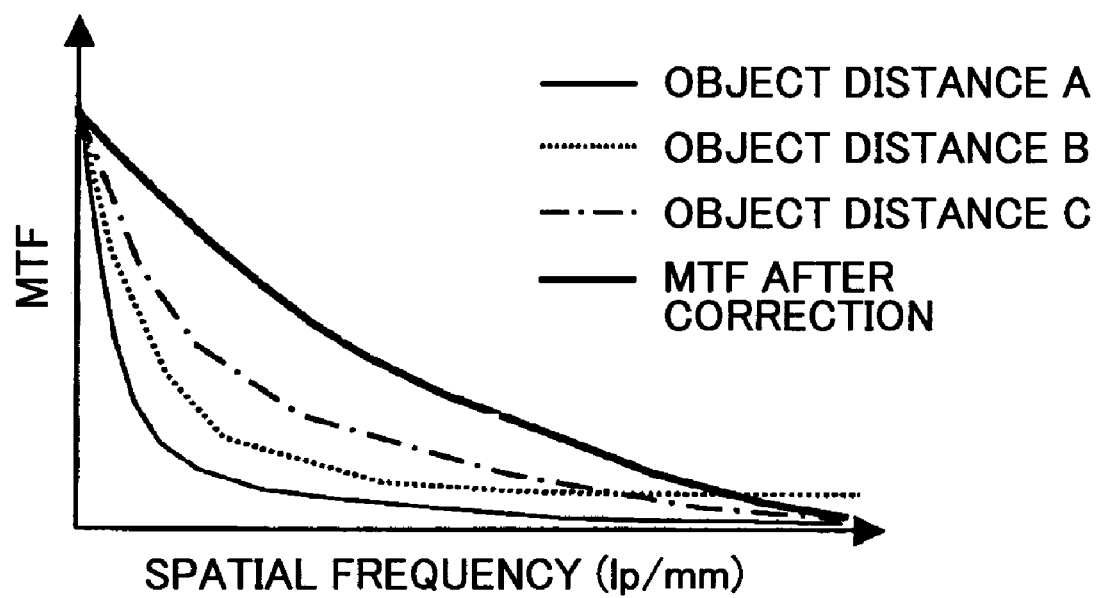
FIG. 11 is a graph illustrating MTF characteristics of a plano-convex lens in relation to the object distance in the case where the convex face of the plano-convex lens faces the image surface side.

FIG. 11 is a graph illustrating exemplary variations in MTF characteristics according to the object distance in a plano-convex lens having its convex face facing the image surface side as in the case of FIG. 10B. Specifically, in FIG. 11, MTF characteristics at a predetermined visual angle when the object distance is equal to A, B, and C are illustrated by a thin solid line, a dotted line, and a dashed line, respectively. As can be appreciated from this example, in a case where variations in the object distance cannot be disregarded (i.e., when MTF characteristics vary depending on the object distance), correction errors may occur when image degradation correction (MTF correction) is performed based on optical transfer function data for a predetermined distance. Thus, in order to reduce correction errors, optical transfer function data for different object distances are preferably prepared beforehand so that the optical transfer function data to be used for image degradation correction may be selected according to the object distance. By performing image degradation correction according to the object distance in the manner described above, image degradation may be appropriately corrected to obtain suitable MTF characteristics as is illustrated by a thick solid line in FIG. 11, for example.

Figure 12:
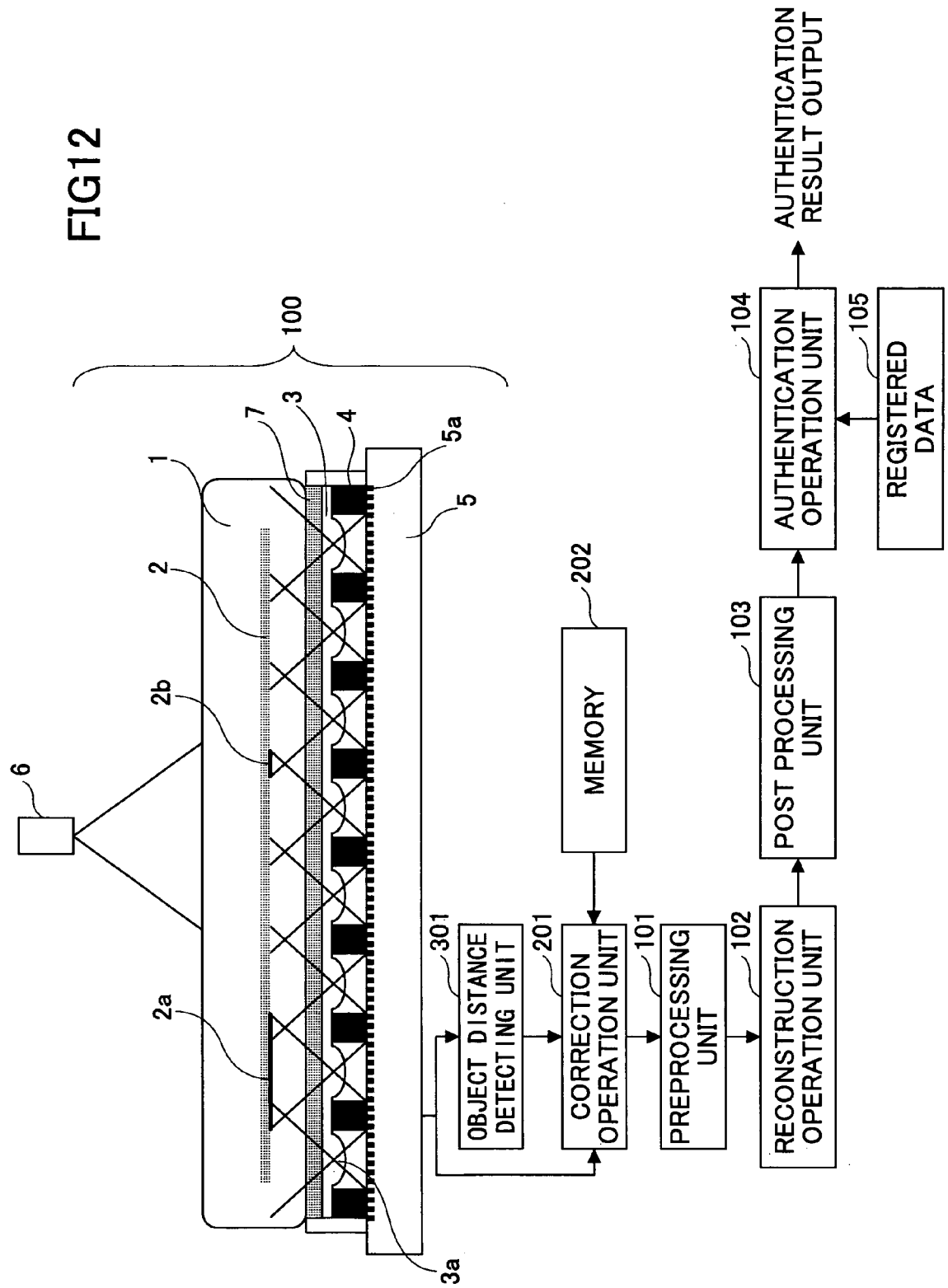
FIG. 12 is a diagram illustrating a third embodiment of the present invention.

FIG. 12 is a diagram showing an image input apparatus and a personal authentication apparatus according to a third embodiment of the present invention. In the present embodiment, an object distance detecting unit 301 is added for detecting the object distance (i.e., distance from the object 2 to the lens array 3). Also, the memory 202 stores optical transfer data for different object distances with respect to the lenses 3a, and the correction operation unit 201 is configured to read the optical transfer function stored in the memory 202 that are associated with an object distance that is closest to the object distance detected by the object distance detecting unit 301 to perform image degradation correction (MTF correction) on each ommatidium image of a compound-eye image using the read optical transfer function data. It is noted that other features of the apparatus according to the present embodiment may be identical to those of the second embodiment.

As is described above in relation to the first embodiment of the present invention, the overlapping regions between ommatidium images may vary depending on the object distance (see FIG. 5). Accordingly, the object distance may be calculated based on the triangulation principle using information on the overlapping regions, namely, the detected parallax. The object distance detecting unit 301 according to the present embodiment employs such a method to detect the object distance. Specifically, the object distance detecting unit 301 detects the parallax between ommatidium images of a compound-eye image that is captured by the image pickup device 5 and calculates the object distance based on the triangulation principle using the detected parallax. It is noted that the object distance may be obtained by detecting the parallax between two ommatidium images; that is, the parallaxes for all the ommatidium images of the compound-eye image are not required for obtaining the object distance. Also, the parallax between ommatidium images may be detected using the detection method as is described above.

According to a modified example of the embodiment shown in FIG. 12, the correction processing part for correcting image degradation caused by the lens 3a (MTF correction) may be arranged to come after the post processing unit 103 rather than before the preprocessing unit 101. Specifically, a correction operation unit may be arranged between the post processing unit 103 and the authentication operation unit 104, and a memory for storing optical transfer function data may be connected to this correction operation unit so that image degradation correction (MTF correction) may be performed on a reconstructed single image using the optical transfer function data associated with the object distance detected by the object distance detecting unit 301. It is noted that correction process with respect to a single image may be completed by performing one correction process sequence on the reconstructed single image so that operation time may be reduced compared to the case of performing correction on each ommatidium image. However, it is noted that since the optical transfer function data to be used in the correction process pertain to the individual lenses 3a and are intended to be used for correcting the individual ommatidium images, when the correction process is performed on the single image rather than the individual ommatidium images, correction errors may inevitably be increased compared to the case of performing correction on the individual ommatidium images.

Fourth Embodiment

Figure 13:
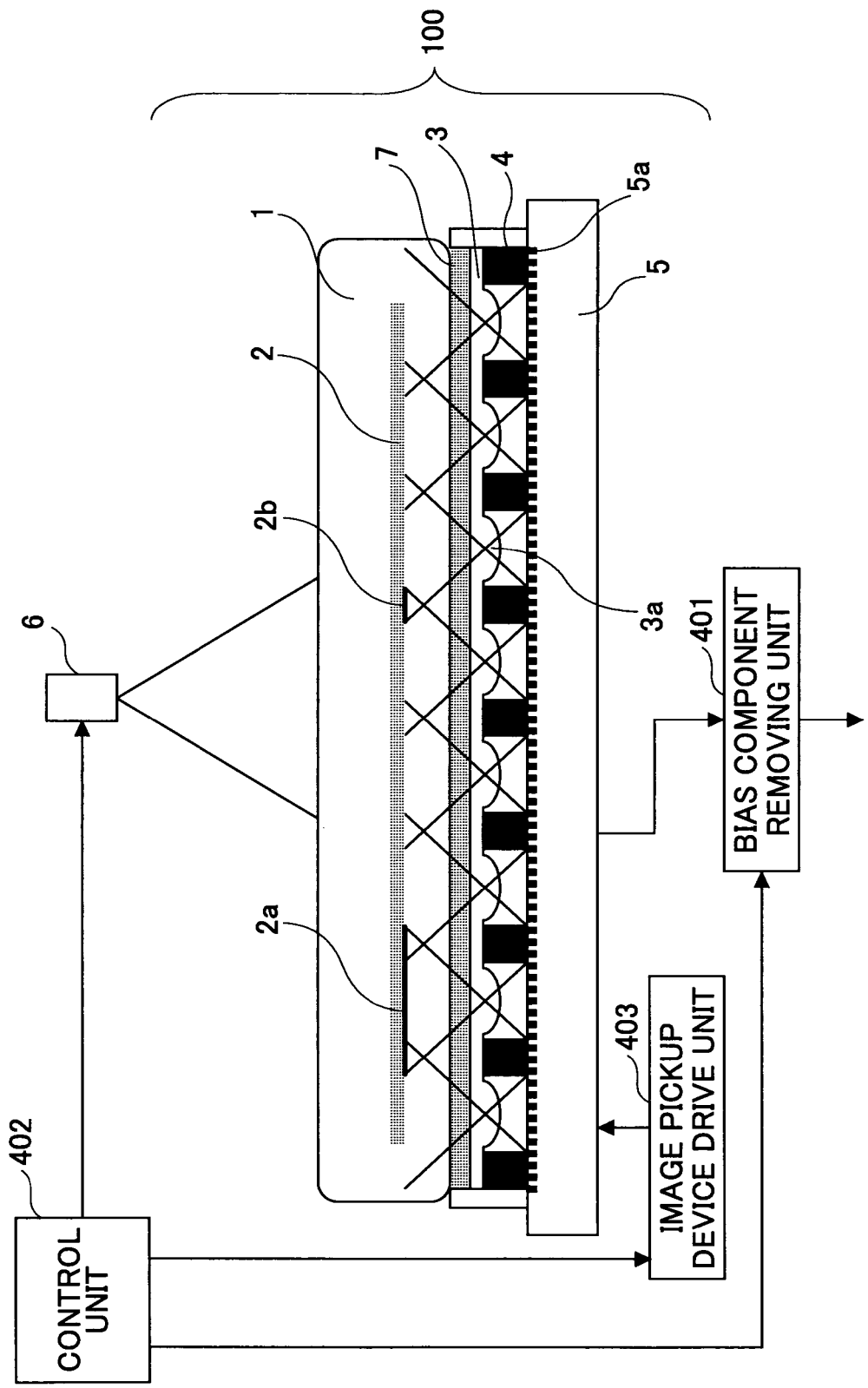
FIG. 13 is a diagram illustrating a fourth embodiment of the present invention.
Figure 14:
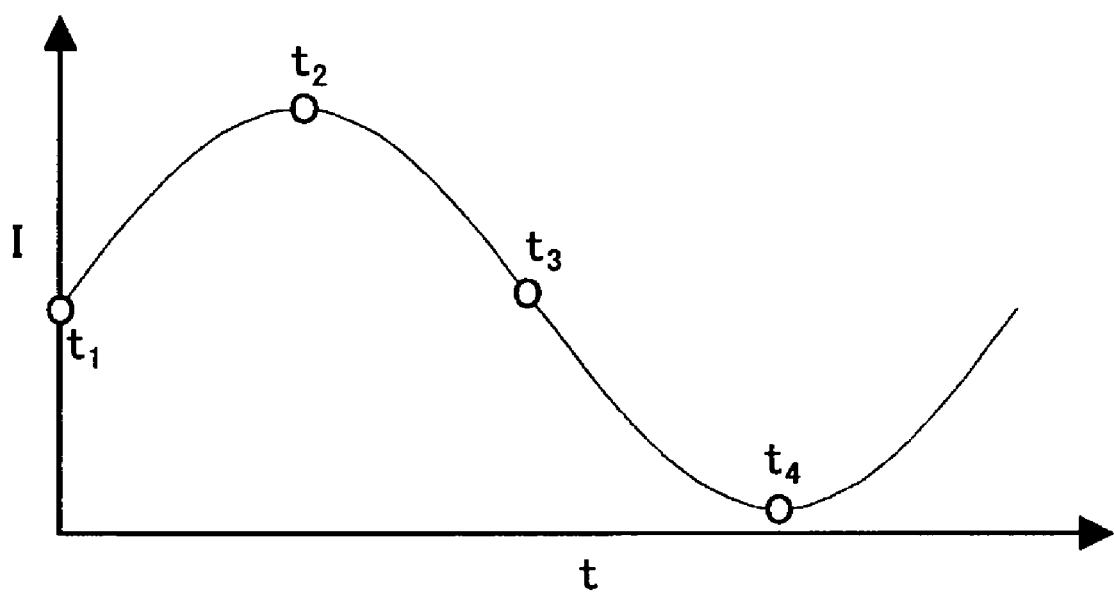
FIG. 14 is a graph illustrating image sampling timings in a case of modulating the intensity of irradiated light into a sine wave, dividing the modulation period into four phases, and sampling images at these phase intervals.

FIG. 13 is a diagram showing an image input apparatus and a personal authentication apparatus according to a fourth embodiment of the present invention. According to the present embodiment, a bias component removing unit 401 and a control unit 402 for controlling drive operations of the light source 6 are used to obtain compound-eye image data having bias components of external light other than the near infrared light irradiated from the light source 6 (bias light) removed therefrom. Also, an image pickup drive unit 403 is used for driving the image pickup device 5. It is noted that other features of the present embodiment may be identical to any one of the previously described embodiments or modifications thereof so that illustrations of such features are omitted in FIG. 13. Also, it is noted that although a band pass filter 7 is included in FIG. 13, such a component may alternatively be omitted. In the case of omitting the band pass filter 7, a transparent plate for adjusting the object distance and/or protecting the lens array 3 may be arranged at the position of the band pass filter 7, for example. Also, it is noted that although the image pickup device unit 403 is not shown in the drawings representing the previously-described embodiments, illustrations of such a component are merely omitted in these drawings and means for driving the image pickup device 5 is used in these embodiments as well.

Example 1

According to a first exemplary implementation of the present embodiment, the control unit 402 turns on/off a drive current for the light source to control the light source 6 to intermittently emit light. In other words, light emission of the light source 6 is intermittently turned on/off. In this case, compound-eye images at emission-on time and emission-off time of the light source 6 are captured by the image pickup device 5, and timing signals in synch with the emission on and off times of the light source 6 are supplied to the image pickup drive unit 403 and the bias component removing unit 401 by the control unit 402 in order to control the bias component removing unit 401 to acquire these compound-eye images. The bias component removing unit 401 obtains a difference between the compound-eye image captured at the light source 6 emission-on time and the compound-eye image captured at the light source 6 emission-off time to remove bias components of external light and generate a compound-eye image that is made up of light components of light emitted from the light source 6.

Example 2

According to a second exemplary implementation of the present embodiment, the control unit 402 modulates the drive current for the light source 6 into a sine wave so that the intensity of the near infrared light irradiated from the light source 6 may be changed according to the sine wave. Since external light (bias light) is superposed on the near infrared light, provided that such lights are directly incident on the image pickup device 5, light intensity modulation as is shown in FIG. 9 may be successively obtained for every pixel. It is noted that the intensity of the pixel at a given image position (x, y) within an image may be expressed by the below formula (5).

$$I(x,y) = A(x,y) + B(x,y) \cdot \cos\{\phi(x,y)\} \qquad (5)$$

In the above formula (5), I denotes the intensity of the given pixel, A denotes the intensity of the external light, namely, the bias light, B denotes the modulation amplitude of the light irradiated by the light source 6, and φ denotes the modulation phase of the light irradiated by the light source 6.

When the modulation period is divided into four time intervals and images are captured at time points t1, t2, t3, and t4 as is shown in FIG. 9, for example, the image intensity of the images obtained at the above time points may be expressed by the below formulae (6)-(9)

$$I_1(x,y) = A(x,y) + B(x,y) \cdot \cos(\phi) \qquad (6)$$

$$I_2(x,y) = A(x,y) + B(x,y) \cdot \sin(\phi) \qquad (7)$$

$$I_3(x,y) = A(x,y) - B(x,y) \cdot \cos(\phi) \qquad (8)$$

$$I_4(x,y) = A(x,y) - B(x,y) \cdot \sin(\phi) \qquad (9)$$

The modulation amplitude of the light irradiated by the light source 6 may be obtained by the below formula (10) using the above formulae (6)-(9). Thus, by computing the below formula (10) using the images captured at the above time points, the bias component removing unit 401 may generate a compound-eye image having bias components removed therefrom.

$$B(x, y) = \frac{I_1(x, y) - I_3(x, y)}{2 \cdot \cos\left\{\frac{I_2(x, y) - I_4(x, y)}{I_1(x, y) - I_3(x, y)}\right\}} \qquad (10)$$

It is noted that in the above-described example, the modulation period is divided into four and images are sampled at the divided time intervals; however, in other alternative implementations, the sampling frequency within the modulation period may be increased, or discrete Fourier transform may be used in the computation for extracting the modulation amplitude, for example. It is noted that when the sampling frequency is increased, bias components may be more accurately removed.

Fifth Embodiment

The overall imaging optical system of a personal authentication apparatus according to an embodiment of the present invention may be arranged into a relatively thin structure so that the authentication apparatus may be readily installed in various electronic apparatuses. In this way, operations of the electronic apparatus may be controlled according to the authentication result obtained by the authentication apparatus and usage of the electronic apparatus may be limited to certain users, for example.

Figure 16A:
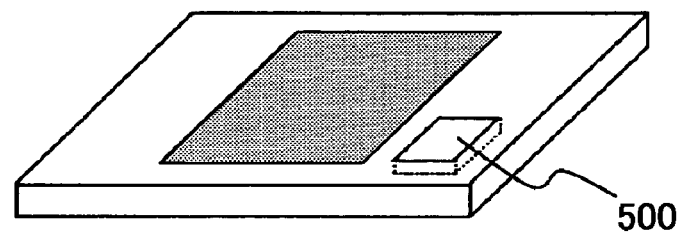
FIGS. 16A and 16B are perspective views of exemplary electronic apparatuses each having a personal authentication apparatus according to an embodiment of the present invention installed therein.
Figure 16B:
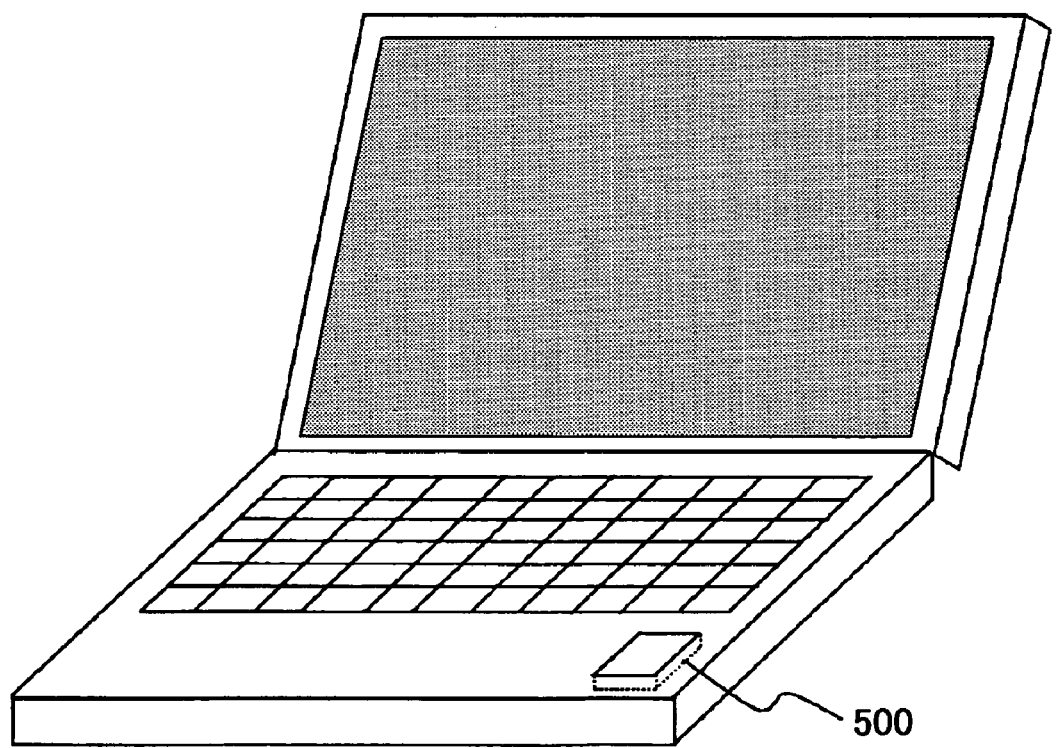

FIGS. 16A and 16B are diagrams showing a miniature information terminal (e.g., PDA) and a laptop computer as exemplary electronic apparatuses each having a personal authentication apparatus 500 according to an embodiment of the present invention installed therein. In the examples of FIGS. 16A and 16B, only a portion of the personal authentication apparatus 500 on which a finger is to be placed (e.g., portion of the optical band pass filter 7) is exposed. A person that wishes to use the information terminal or the laptop computer may place his/her finger on the exposed portion of the personal authentication apparatus 500 to have the vein pattern of his/her finger read and authenticated by the personal authentication apparatus 500. The electronic apparatus (i.e., the information terminal or the laptop computer) may control user access by allowing the person to login when the person is authenticated as a registered user while refusing to let the person login when the person is not authenticated as a registered user.

(Miscellaneous)

According to certain embodiments, the reconstruction operation unit, the correction operation unit, the object distance detecting unit, the bias component removing unit, and the authentication processing unit of used in the above-described first though fourth embodiments may be configured, at least in part, by software.

Also, the above-described operations of the image input apparatus according to the first through fourth embodiments may be construed as image input methods according to embodiments of the present invention.

In the following, overall descriptions of possible embodiments of the present invention and their advantageous effects are given.

According to a first aspect of the present invention, an image input apparatus is provided that inputs an image of an object residing within a living body, the apparatus including:
a light source that irradiates near infrared light on the living body;
a lens array that is arranged at a position facing the living body and includes plural lenses each having a face with zero or negative power arranged at a side facing the living body and a face with positive power arranged at a side facing an image surface;
an imaging unit that is arranged at the image surface side of the lens array and is configured to form a compound-eye image corresponding to a collection of ommatidium images formed by the lenses of the lens array; and
a reconstruction unit that is configured to reconstruct a single image from the compound-eye image formed by the imaging unit using a parallax between the ommatidium images, the reconstructed single image being input as the image of the object.

According to a second aspect of the present invention, an image input apparatus is provided that inputs an image of an object residing within a living body, the apparatus comprising:
a light source that irradiates near infrared light on the living body;
a lens array that is arranged at a position facing the living body and includes plural lenses each having a face with zero or negative power at a side facing the living body and a face with positive power at a side facing an image surface;
an imaging unit that is arranged on the image surface side of the lens array and is configured to form a compound-eye image corresponding to a collection of ommatidium images formed by the lenses of the lens array;
a correction unit that is configured to correct image degradation caused by the lenses in the ommatidium images of the compound-eye image formed by the imaging unit based on optical transfer function data pertaining to the lenses that are prepared beforehand and generate a corrected compound-eye image; and
a reconstruction unit that is configured to reconstruct a single image from the corrected compound-eye image generated by the correction unit using a parallax between the ommatidium images, the reconstructed single image being input as the image of the object.

According to a third aspect of the present invention, an image input apparatus is provided that inputs an image of an object residing within a living body, the apparatus including:
a light source that irradiates near infrared light on the living body;
a lens array that is arranged at a position facing the living body and includes plural lenses each having a face with zero or negative power arranged at a side facing the living body and a face with positive power arranged at a side facing an image surface;
an imaging unit that is arranged at the image surface side of the lens array and is configured to form a compound-eye image corresponding to a collection of ommatidium images formed by the lenses of the lens array;
a reconstruction unit that is configured to reconstruct a single image from the compound-eye image formed by the imaging unit using a parallax between the ommatidium images; and
a correction unit that is configured to correct image degradation caused by the lenses in the reconstructed single image based on optical transfer function data pertaining to the lenses that are prepared beforehand, the corrected single image being input as the image of the object.

According to a fourth aspect of the present invention, the above-described image input apparatuses according to the first through third aspects of the present invention may further include:
an optical band pass filter that is configured to pass light having a wavelength within a predetermined wavelength range including a wavelength of the near infrared light irradiated by the light source, the optical band pass filter being arranged at the living body side or the image surface side of the lens array.

According to a fifth aspect of the present invention, an image input apparatus is provided that inputs an image of an object residing within a living body, the apparatus including:
a light source that irradiates near infrared light on the living body;
a control unit that controls light irradiation by the light source to be turned on/off;
a lens array that is arranged at a position facing the living body and includes plural lenses each having a face with zero or negative power arranged at a side facing the living body and a face with positive power arranged at a side facing an image surface;

an imaging unit that is arranged at the image surface side of the lens array and is configured to form a compound-eye image corresponding to a collection of ommatidium images formed by the lenses of the lens array;

a bias component removing unit that is configured to obtain a difference between a compound-eye image formed by the imaging unit when the light source is turned on and a compound-eye image formed by the imaging unit when the light source is turned off and generate a bias-removed compound-eye image having a bias component of light other than the near infrared light irradiated by the light source removed therefrom; and a reconstruction unit that is configured to reconstruct a single image from the bias-removed compound-eye image generated by the bias component removing unit using a parallax between the ommatidium images, the reconstructed single image being input as the image of the object.

According to a sixth aspect of the present invention, an image input apparatus is provided that inputs an image of an object residing within a living body, the apparatus comprising:

a light source that irradiates near infrared light on the living body;

a control unit that controls light irradiation by the light source to be turned on/off;

a lens array that is arranged at a position facing the living body and includes plural lenses each having a face with zero or negative power at a side facing the living body and a face with positive power at a side facing an image surface;

an imaging unit that is arranged on the image surface side of the lens array and is configured to form a compound-eye image corresponding to a collection of ommatidium images formed by the lenses of the lens array;

a bias component removing unit that is configured to obtain a difference between a compound-eye image formed by the imaging unit when the light source is turned on and a compound-eye image formed by the imaging unit when the light source is turned off and generate a bias-removed compound-eye image having a bias component of light other than the near infrared light irradiated by the light source removed therefrom;

a correction unit that is configured to correct image degradation caused by the lenses in the ommatidium images of the bias-removed compound-eye image generated by the bias component removing unit based on optical transfer function data pertaining to the lenses that are prepared beforehand and generate a corrected compound-eye image; and a reconstruction unit that is configured to reconstruct a single image from the corrected compound-eye image generated by the correction unit using a parallax between the ommatidium images, the reconstructed single image being input as the image of the object.

According to a seventh aspect of the present invention, an image input apparatus is provided that inputs an image of an object residing within a living body, the apparatus including:

a light source that irradiates near infrared light on the living body;

a control unit that controls light irradiation by the light source to be turned on/off;

a lens array that is arranged at a position facing the living body and includes plural lenses each having a face with zero or negative power arranged at a side facing the living body and a face with positive power arranged at a side facing an image surface;

an imaging unit that is arranged at the image surface side of the lens array and is configured to form a compound-eye image corresponding to a collection of ommatidium images formed by the lenses of the lens array;

a bias component removing unit that is configured to obtain a difference between a compound-eye image formed by the imaging unit when the light source is turned on and a compound-eye image formed by the imaging unit when the light source is turned off and generate a bias-removed compound-eye image having a bias component of light other than the near infrared light irradiated by the light source removed therefrom;

a reconstruction unit that is configured to reconstruct a single image from the bias-removed compound-eye image formed by the bias component removing unit using a parallax between the ommatidium images; and a correction unit that is configured to correct image degradation caused by the lenses in the reconstructed single image based on optical transfer function data pertaining to the lenses that are prepared beforehand, the corrected single image being input as the image of the object.

According to an eighth aspect of the present invention, an image input apparatus is provided that inputs an image of an object residing within a living body, the apparatus including:

a light source that irradiates near infrared light on the living body;

a control unit that changes an intensity of the near infrared light irradiated on the living body by the light source into a sine wave;

a lens array that is arranged at a position facing the living body and includes plural lenses each having a face with zero or negative power arranged at a side facing the living body and a face with positive power arranged at a side facing an image surface;

an imaging unit that is arranged at the image surface side of the lens array and is configured to form a compound-eye image corresponding to a collection of ommatidium images formed by the lenses of the lens array;

a bias component removing unit that is configured to perform computation processes on plural compound-eye images formed by the imaging unit at plural different phase points within a sine wave change period of the intensity of the near infrared light irradiated on the living body by the light source and generate a bias-removed compound-eye image having a bias component of light other than the near infrared light irradiated by the light source removed therefrom; and a reconstruction unit that is configured to reconstruct a single image from the bias-removed compound-eye image generated by the bias component removing unit using a parallax between the ommatidium images, the reconstructed single image being input as the image of the object.

According to a ninth aspect of the present invention, an image input apparatus is provided that inputs an image of an object residing within a living body, the apparatus comprising:

a light source that irradiates near infrared light on the living body;

a control unit that changes an intensity of the near infrared light irradiated on the living body by the light source into a sine wave;

a lens array that is arranged at a position facing the living body and includes plural lenses each having a face with zero or negative power at a side facing the living body and a face with positive power at a side facing an image surface;

an imaging unit that is arranged on the image surface side of the lens array and is configured to form a compound-eye image corresponding to a collection of ommatidium images formed by the lenses of the lens array;

a bias component removing unit that is configured to perform computation processes on plural compound-eye images formed by the imaging unit at plural different phase points within a sine wave change period of the intensity of the near infrared light irradiated on the living body by the light source and generate a bias-removed compound-eye image having a bias component of light other than the near infrared light irradiated by the light source removed therefrom;

a correction unit that is configured to correct image degradation caused by the lenses in the ommatidium images of the bias-removed compound-eye image generated by the bias component removing unit based on optical transfer function data pertaining to the lenses that are prepared beforehand and generate a corrected compound-eye image; and a reconstruction unit that is configured to reconstruct a single image from the corrected compound-eye image generated by the correction unit using a parallax between the ommatidium images, the reconstructed single image being input as the image of the object.

According to a tenth aspect of the present invention, an image input apparatus is provided that inputs an image of an object residing within a living body, the apparatus including:

a light source that irradiates near infrared light on the living body;

a control unit that changes an intensity of the near infrared light irradiated on the living body by the light source into a sine wave;

a lens array that is arranged at a position facing the living body and includes plural lenses each having a face with zero or negative power arranged at a side facing the living body and a face with positive power arranged at a side facing an image surface;

an imaging unit that is arranged at the image surface side of the lens array and is configured to form a compound-eye image corresponding to a collection of ommatidium images formed by the lenses of the lens array;

a bias component removing unit that is configured to perform computation processes on plural compound-eye images formed by the imaging unit at plural different phase points within a sine wave change period of the intensity of the near infrared light irradiated on the living body by the light source and generate a bias-removed compound-eye image having a bias component of light other than the near infrared light irradiated by the light source removed therefrom;

a reconstruction unit that is configured to reconstruct a single image from the bias-removed compound-eye image formed by the bias component removing unit using a parallax between the ommatidium images; and a correction unit that is configured to correct image degradation caused by the lenses in the reconstructed single image based on optical transfer function data pertaining to the lenses that are prepared beforehand, the corrected single image being input as the image of the object. the image input apparatus as claimed in claim 1, further comprising:

a transparent plate for adjusting a distance between the object and the lens array which transparent plate is arranged at the living body side of the lens array.

According to an eleventh aspect of the present invention, the above-described image input apparatuses according to the second, third, sixth, seventh, ninth and tenth aspects of the present invention may further include:

a distance detecting unit that is configured to detect a distance between the object and the lens array; and the correction unit may select a set of optical transfer function data from the optical transfer function data pertaining to the lenses that are prepared beforehand according to the distance detected by the distance detecting unit and use the selected set of optical transfer function data for correcting the image degradation caused by the lenses.

According to a twelfth aspect of the present invention, in the above-described image input apparatus according to the eleventh aspect, the distance detecting unit may detect the distance based on the parallax between the ommatidium images of the compound-eye image formed by the imaging unit.

According to a thirteenth aspect of the present invention, the above-described image input apparatuses according to the first through twelfth aspects may further include:

a transparent plate for adjusting a distance between the object and the lens array which transparent plate is arranged at the living body side of the lens array.

According to a fourteenth embodiment of the present invention, the above described image input apparatuses according to the first through thirteenth aspects may further include:

a light shielding member that prevents occurrence of crosstalk between the lenses of the lens array at the image surface side.

According to a fifteenth aspect of the present invention, a personal authentication apparatus is provided that includes any one of the image input apparatuses according to the first through fourteenth aspects of the present invention, and an authentication unit that performs personal authentication based on the image of the object input by the image inputting apparatus.

According to a sixteenth aspect of the present invention, an electronic apparatus is provided that includes the above-described personal authentication apparatus according to the fifteenth aspect of the present invention, the operations of the electronic apparatus being controlled according to an authentication result obtained by the personal authentication apparatus.

According to a seventeenth aspect of the present invention, an image input method is provided for inputting an image of an object residing within a living body, the method including the steps of:

using an imaging optical system that includes
a light source that irradiates near infrared light on the living body;
a lens array that is arranged at a position facing the living body and includes a plurality of lenses, each of the lenses having a face with zero or negative power at a side facing the living body and a face with positive power at a side facing an image surface; and
an imaging unit that is arranged on the image surface side of the lens array and is configured to form a compound-eye image corresponding to a collection of ommatidium images formed by the lenses of the lens array;

correcting image degradation caused by the lenses in the ommatidium images of the compound-eye image formed by the imaging unit based on optical transfer function data pertaining to the lenses that are prepared beforehand to generate a corrected compound-eye image;

reconstructing a single image from the corrected compound-eye image using a parallax between the ommatidium images; and inputting the reconstructed single image as the image of the object.

According to an eighteenth aspect of the present invention, an image input method is provided for inputting an image of an object residing within a living body, the method including the steps of:

using an imaging optical system that includes
  a light source that irradiates near infrared light on the living body;
  a lens array that is arranged at a position facing the living body and includes a plurality of lenses, each of the lenses having a face with zero or negative power at a side facing the living body and a face with positive power at a side facing an image surface; and
  an imaging unit that is arranged on the image surface side of the lens array and is configured to form a compound-eye image corresponding to a collection of ommatidium images formed by the lenses of the lens array;
controlling the light source to irradiate light intermittently;
obtaining a difference between a compound-eye image formed by the imaging unit when the light source is turned on and a compound-eye image formed by the imaging unit when the light source is turned off to generate a bias-removed compound-eye image having bias components of light other than the near infrared light irradiated by the light source removed therefrom;
correcting image degradation caused by the lenses in the ommatidium images of the bias-removed compound-eye image based on optical transfer function data pertaining to the lenses that are prepared beforehand to generate a corrected compound-eye image;
reconstructing a single image from the corrected compound-eye image using a parallax between the ommatidium images; and
inputting the reconstructed single image as the image of the object.

According to a nineteenth aspect of the present invention, an image input method is provided for inputting an image of an object residing within a living body, the method including the steps of:
using an imaging optical system that includes
  a light source that irradiates near infrared light on the living body;
  a lens array that is arranged at a position facing the living body and includes a plurality of lenses, each of the lenses having a face with zero or negative power at a side facing the living body and a face with positive power at a side facing an image surface; and
  an imaging unit that is arranged on the image surface side of the lens array and is configured to form a compound-eye image corresponding to a collection of ommatidium images formed by the lenses of the lens array;
changing the intensity of the near infrared light irradiated by the light source into a sine wave;
performing computation processes on plural compound-eye images formed by the imaging unit at plural different phase points within a sine wave change period of the intensity of the near infrared light irradiated by the light source to generate a bias-removed compound-eye image having bias components of light other than the near infrared light irradiated by the light source removed therefrom;
correcting image degradation caused by the lenses in the ommatidium images of the bias-removed compound-eye image based on optical transfer function data pertaining to the lenses that are prepared beforehand to generate a corrected compound-eye image;
reconstructing a single image from the corrected compound-eye image using a parallax between the ommatidium images; and
inputting the reconstructed single image as the image of the object.

According to the first through fourteenth aspects of the present invention, the imaging optical system including the light source, the lens array, and the imaging unit may be arranged into a relatively thin and simple structure so that the overall thickness of the image input apparatus may be reduced, for example.

Also, since near infrared light, which is absorbed at a high absorption rate by an imaging object such as veins residing within the living body but is hardly absorbed by portions of the living body other than the imaging object, is irradiated on the living body by the light source, a clear image of the imaging object such as veins may be formed. Also, it is noted that in a compound-eye optical system, normally, a face of a lens of a lens array with positive power (e.g., convex face of a plano-convex lens) is arranged to face the imaging object side. However, in embodiments of the present invention, a lens having a face with zero or negative power arranged at the object side and a face with positive power arranged at the image surface side (e.g., plano-concave lens having a concave face facing the image surface side) is used as the lenses of a lens array so that even when the object distance is small, variations in the MTF due to variations in the object visual angle (angle of incidence of light incident to the lens) may be reduced, and occurrence of in-plane errors such as distortions and curvatures may be prevented, for example. Further, it is noted that the object distance may vary depending on the skin thickness of each person, for example. However, the process of reconstructing a single image from a compound-eye image using the parallax between ommatidium images according to embodiments of the present invention may easily adapt to variations in the object distance and compensate for a decrease in the image resolution, for example. In this way, a high quality image of an imaging object such as veins within a living body may be input.

Further, by correcting a compound-eye image by performing correction processes on the individual ommatidium images of the compound-eye image based on the optical transfer function data of the lenses as in the second, sixth, and ninth aspects of the present invention, or correcting a single image reconstructed from a compound-eye image based on such optical transfer function data as in the third, seventh, and tenth aspects of the present invention, an even higher quality image in which image degradation caused by the lenses are corrected may be input. Also, by enabling selection of the optical transfer function data to be used in the image degradation correction process according to the object distance as in the eleventh aspect of the present invention, image degradation correction may be accurately performed even when the object distance varies. In this way, influences caused by differences in the object distance may be reduced, and the input image quality may be further improved. Also, by using a lens having a face with zero or negative power arranged at the object side and a face with positive power arranged at the image surface side as the lenses of the lens array, variations in the MTF due to variations in the object visual angle (angle of incidence of light incident to the lens) may be reduced so that the image degradation correction process may be simplified, for example.

By arranging an optical band pass filter that only passes light having a wavelength within a predetermined wavelength range including the wavelength of the near infrared light irradiated by the light source as in the fourth aspect of the present invention, or by removing bias components through light source modulation and computation processes as in the fifth through tenth aspects of the present invention, influences of external light, namely, light other than the irradiation light from the light source, may be reduced, and a stable image of the object may be input, for example.

In a case where the object is positioned too close to the lens array so that overlapping image regions do not exist between adjacent ommatidium images, image reconstruction using the parallax between the ommatidium images may not be effectively performed. Such a problem may be prevented by arranging a transparent plate for adjusting the distance between the object and the lens array as in the thirteenth aspect of the present invention, for example.

Also, by including a light shielding member as in the fourteenth aspect of the present invention, cross talk between the lenses of the lens array at the image surface side may be prevented so that noise such as ghosts and flares may be reduced in the input image, for example.

According to the fifteenth aspect of the present invention, by using a thin image input apparatus with a simple configuration according to an aspect of the present invention, a thin personal authentication apparatus that is suitable for installation in an electronic apparatus may be realized, for example.

According to the sixteenth aspect of the present invention, by installing a personal authentication apparatus according to an aspect of the present invention into an electronic apparatus, enlargement of the electronic apparatus due to installation of the personal authentication apparatus may not be necessary, for example.

Also, login access to an electronic apparatus such as a miniature information terminal or a laptop computer may be controlled according to authentication results obtained by the personal authentication apparatus so that security of the electronic apparatus may be improved, for example.

According to the seventeenth through nineteenth aspects of the present invention, advantageous effects similar to those obtained in the first through fourteenth aspects of the present invention may be obtained. For example, by implementing an image input method according an aspect of the present invention, a high quality image of an object such as veins within a living body may be input, and/or a stable image that is not readily influenced by light other than irradiation light from the light source may be input.

Although the present invention is shown and described with respect to certain preferred embodiments, it is obvious that equivalents and modifications will occur to others skilled in the art upon reading and understanding the specification. The present invention includes all such equivalents and modifications, and is limited only by the scope of the claims.

The present application is based on and claims the benefit of the earlier filing date of Japanese Patent Application No. 2006-278423 filed on Oct. 12, 2006, the entire contents of which are hereby incorporated by reference.

The invention claimed is:

1. An image input apparatus that inputs an image of an object residing within a living body, the apparatus comprising:
   a light source that irradiates near infrared light on the living body;
   a lens array that is arranged at a position facing the living body and includes a plurality of lenses, each of the lenses having a face with zero or negative power arranged at a side facing the living body and a face with positive power arranged at a side facing an image surface;
   an imaging unit that is arranged at the image surface side of the lens array and is configured to form a compound-eye image corresponding to a collection of ommatidium images formed by the lenses of the lens array;
   a bias component removal processing unit that is configured to generate a compound-eye image in which a bias component, due to light other than the near infrared light irradiated by the light source, is removed, the bias component being generated based on a difference between a compound-eye image formed by the imaging unit while the light source is turned ON and a compound-eye image is formed by the imaging unit while the light source is turned OFF; and
   a reconstruction unit that is configured to select a reference ommatidium image, obtain parallaxes of the ommatidium images with respect to the reference ommatidium image, and reconstruct the ommatidium images from the compound-eye image generated by the bias component removal processing unit based on the obtained parallaxes, said reconstructed ommatidium images being input as the image of the object.

2. The image input apparatus as claimed in claim 1, further comprising:
   an optical band pass filter that is configured to pass light having a wavelength within a predetermined wavelength range including a wavelength of the near infrared light irradiated by the light source, said optical band pass filter being arranged at the living body side or the image surface side of the lens array.

3. The image input apparatus as claimed in claim 1, further comprising:
   a transparent plate for adjusting a distance between the object and the lens array wherein the transparent plate is arranged at the living body side of the lens array.

4. The image input apparatus as claimed in claim 1, further comprising:
   a light shielding member that prevents occurrence of crosstalk between the lenses of the lens array at the image surface side.

5. An image input apparatus that inputs an image of an object residing within a living body, the apparatus comprising:
   a light source that irradiates near infrared light on the living body;
   a lens array that is arranged at a position facing the living body and includes a plurality of lenses, each of the lenses having a face with zero or negative power at a side facing the living body and a face with positive power at a side facing an image surface;
   an imaging unit that is arranged on the image surface side of the lens array and is configured to form a compound-eye image corresponding to a collection of ommatidium images formed by the lenses of the lens array;
   a bias component removal processing unit is configured to generate a compound-eye image in which a bias component, due to light other than the near infrared light irradiated by the light source, is removed, the bias component being generated based on a difference between a compound-eye image formed by the imaging unit while the light source is turned ON and a compound-eye image formed by the imaging unit while the light source is turned OFF;
   a correction unit is configured to correct image degradation caused by the lenses in the ommatidium images of the compound-eye image generated by the bias component removal processing unit based on optical transfer function data pertaining to the lenses that are prepared beforehand and generate a corrected compound-eye image; and
   a reconstruction unit that is configured to select a reference ommatidium image, obtain parallaxes of the ommatidium images with respect to the reference ommatidium image, and reconstruct the ommatidium images from the corrected compound-eye image generated by the correction unit based on the obtained parallaxes, said reconstructed ommatidium images being input as the image of the object.

6. The image input apparatus as claimed in claim 5, further comprising:
an optical band pass filter that is configured to pass light having a wavelength within a predetermined wavelength range including a wavelength of the near infrared light irradiated by the light source, said optical band pass filter being arranged at the living body side or the image surface side of the lens array.

7. The image input apparatus as claimed in claim 5, further comprising:
a distance detecting unit that is configured to detect a distance between the living body and the lens array;
wherein the correction unit selects a set of optical transfer function data from the optical transfer function data pertaining to the lenses that are prepared beforehand according to the distance detected by the distance detecting unit and uses the selected set of optical transfer function data for correcting the image degradation caused by the lenses.

8. The image input apparatus as claimed in claim 7, wherein
the distance detecting unit detects the distance based on the parallax between the ommatidium images of the compound-eye image formed by the imaging unit.

9. The image input apparatus as claimed in claim 5, further comprising:
a transparent plate for adjusting a distance between the object and the lens array wherein the transparent plate is arranged at the living body side of the lens array.

10. The image input apparatus as claimed in claim 5, further comprising:
a light shielding member that prevents occurrence of crosstalk between the lenses of the lens array at the image surface side.

11. An image input method for inputting an image of an object residing within a living body, using an imaging optical system that includes: a light source that irradiates near infrared light on the living body, a lens array that is arranged at a position facing the living body and includes a plurality of lenses, each of the lenses having a face with zero or negative power at a side facing the living body and a face with positive power at a side facing an image surface, and an imaging unit that is arranged on the image surface side of the lens array and is configured to form a compound-eye image corresponding to a collection of ommatidium images formed by the lenses of the lens array, the method comprising:
generating, using a bias component removal processing unit, a compound-eye image in which a bias component, due to light other than the near infrared light irradiated by the light source, is removed, the bias component being generated based on a difference between a compound-eye image formed by the imaging unit while the light source is turned ON and a compound-eye image formed by the imaging unit while the light source is turned OFF;
correcting image degradation caused by the lenses in the ommatidium images of the compound-eye image formed by the generated by the bias component removal processing unit based on optical transfer function data pertaining to the lenses that are prepared beforehand to generate a corrected compound-eye image;
selecting a reference ommatidium image;
obtaining parallaxes of the ommatidium images with respect to the reference ommatidium image;
reconstructing the ommatidium images from the corrected compound-eye image based on the obtained parallaxes; and inputting the reconstructed ommatidium images as the image of the object.

* * * * *